(12) United States Patent
Diodati et al.

(10) Patent No.: US 7,918,243 B2
(45) Date of Patent: Apr. 5, 2011

(54) CONNECTOR ASSEMBLY

(75) Inventors: Anthony Diodati, Mullica Hill, NJ (US); Albert A. Werth, Kewadin, MI (US); Clemens E. Zoellner, Bay City, MI (US); Anthony Pagliaro, Lansdale, PA (US); Jeffrey D. Chase, Greenwood, IN (US)

(73) Assignee: Saint-Gobain Performance Plastics Corporation, Aurora, OH (US)

( * ) Notice: Subject to any disclaimer, the term of this patent is extended or adjusted under 35 U.S.C. 154(b) by 17 days.

(21) Appl. No.: 12/410,175

(22) Filed: Mar. 24, 2009

(65) Prior Publication Data
US 2009/0232586 A1   Sep. 17, 2009

Related U.S. Application Data

(63) Continuation-in-part of application No. 12/024,811, filed on Feb. 1, 2008.

(60) Provisional application No. 61/039,311, filed on Mar. 25, 2008, provisional application No. 60/887,751, filed on Feb. 1, 2007.

(51) Int. Cl.
*F16L 37/28* (2006.01)
(52) U.S. Cl. ............... 137/614.03; 137/614.05
(58) Field of Classification Search ........... 137/614.03–614.06, 614; 604/256, 604/905, 167, 169
See application file for complete search history.

(56) References Cited

U.S. PATENT DOCUMENTS

| | | |
|---|---|---|
| 3,837,687 A | 9/1974 | Leonard |
| 3,865,411 A | 2/1975 | Rowe et al. |
| 3,973,791 A | 8/1976 | Porta et al. |
| 4,019,512 A | 4/1977 | Tenczar |
| 4,022,205 A | 5/1977 | Tenczar |
| 4,030,494 A | 6/1977 | Tenczar |
| 4,099,748 A | 7/1978 | Kavick |
| 4,201,208 A | 5/1980 | Cambio, Jr. |
| 4,256,106 A * | 3/1981 | Shoor ..................... 604/905 |
| 4,277,091 A | 7/1981 | Hunter |
| 4,280,722 A | 7/1981 | Guptil et al. |
| 4,285,228 A | 8/1981 | Gunning |
| 4,330,924 A | 5/1982 | Kushner et al. |

(Continued)

FOREIGN PATENT DOCUMENTS

EP   0795342 A   9/1997

(Continued)

OTHER PUBLICATIONS

Written Opinion and International Search Report from related PCT Application; PCT/US2009/038103; 5 pages.

(Continued)

*Primary Examiner* — Kevin L Lee
(74) *Attorney, Agent, or Firm* — Larson Newman & Abel, LLP; Robert T. Conway

(57) ABSTRACT

A sterile connector assembly for mounting on a fluid system includes a first connector and a second connector. The first connector includes a stem defining a fluid passage therethrough, a first housing surrounding the stem and defining a first aperture, and a first valve disposed over the first aperture. The second connector includes a second housing configured to matingly engage the first housing. The second housing defines a second aperture and defines a seal structure. The seal structure is configured to engage the stem. The second connector also includes a second valve disposed over the second aperture. The second valve is configured to engage the first valve when the first housing engages the second housing.

17 Claims, 15 Drawing Sheets

U.S. PATENT DOCUMENTS

| | | |
|---|---|---|
| 4,334,537 A | 6/1982 | Peterson |
| 4,334,551 A * | 6/1982 | Pfister .................... 137/614.03 |
| 4,371,199 A | 2/1983 | Kushner et al. |
| 4,418,945 A | 12/1983 | Kellogg |
| 4,423,732 A | 1/1984 | Tarjan et al. |
| 4,620,662 A | 11/1986 | Driggers |
| 4,717,388 A * | 1/1988 | Steer et al. .................... 604/905 |
| 4,828,160 A | 5/1989 | Sundholm |
| 4,946,200 A | 8/1990 | Blenkush et al. |
| 4,993,756 A | 2/1991 | Bechu |
| 5,067,950 A | 11/1991 | Broadnax, Jr. |
| 5,087,086 A | 2/1992 | Snedeker |
| 5,122,123 A | 6/1992 | Vaillancourt |
| 5,131,696 A | 7/1992 | Sykes et al. |
| 5,380,049 A | 1/1995 | Smowton |
| 5,393,101 A | 2/1995 | Matkovich |
| 5,404,632 A | 4/1995 | Zaborszki |
| 5,492,147 A * | 2/1996 | Challender et al. ...... 137/614.05 |
| 5,499,439 A | 3/1996 | Zaborszki et al. |
| 5,511,720 A | 4/1996 | Zaborszki et al. |
| 5,535,771 A * | 7/1996 | Purdy et al. .................... 604/256 |
| 5,638,869 A | 6/1997 | Zaborszki et al. |
| 5,688,254 A | 11/1997 | Lopez et al. |
| 5,769,558 A | 6/1998 | Jekielek |
| 5,788,433 A | 8/1998 | Grund et al. |
| 5,810,398 A | 9/1998 | Matkovich |
| 5,931,510 A | 8/1999 | Mathew et al. |
| 6,022,053 A | 2/2000 | Hukuda |
| 6,106,027 A | 8/2000 | Mulvey et al. |
| 6,193,282 B1 | 2/2001 | Assenheimer |
| 6,341,802 B1 | 1/2002 | Matkovich |
| 6,394,506 B1 | 5/2002 | Street |
| 6,488,320 B1 * | 12/2002 | Anderson ................ 137/614.05 |
| 6,536,805 B2 | 3/2003 | Matkovich |
| 6,604,758 B1 | 8/2003 | Assenheimer |
| 6,655,655 B1 | 12/2003 | Matkovich et al. |
| 6,874,522 B2 | 4/2005 | Anderson et al. |
| 6,880,801 B2 | 4/2005 | Matkovich et al. |
| 7,090,191 B2 | 8/2006 | Matkovich et al. |
| 7,137,974 B2 | 11/2006 | Almasian et al. |
| 7,358,505 B2 * | 4/2008 | Woodworth et al. ..... 250/455.11 |
| 7,396,051 B2 * | 7/2008 | Baldwin et al. ............... 604/256 |
| 2003/0127851 A1 | 7/2003 | Guslick et al. |
| 2004/0034328 A1 | 2/2004 | Unger et al. |
| 2004/0251683 A1 | 12/2004 | Fisher et al. |
| 2005/0015075 A1 | 1/2005 | Wright et al. |
| 2005/0082826 A1 | 4/2005 | Werth |
| 2005/0090797 A1 | 4/2005 | Almasian et al. |
| 2006/0142735 A1 | 6/2006 | Whitley |
| 2006/0217671 A1 | 9/2006 | Peppel |
| 2007/0276356 A1 | 11/2007 | Downing et al. |

FOREIGN PATENT DOCUMENTS

| | | |
|---|---|---|
| EP | 0966985 A | 12/1999 |
| EP | 1096193 A2 | 5/2001 |
| EP | 0719970 B1 | 8/2001 |
| EP | 1162399 A2 | 12/2001 |
| EP | 1184613 A2 | 3/2002 |
| EP | 0739469 B1 | 10/2002 |
| EP | 1326044 A2 | 7/2003 |
| WO | 90/10816 | 9/1990 |
| WO | 91/02185 | 2/1991 |
| WO | 92/16987 | 10/1992 |
| WO | 9408173 A1 | 4/1994 |
| WO | 98/04468 | 2/1998 |
| WO | 01/14781 A1 | 3/2001 |
| WO | 02/061323 A1 | 8/2002 |
| WO | 2005/019566 A2 | 3/2005 |
| WO | 2005/019718 A1 | 3/2005 |

OTHER PUBLICATIONS

U.S. Appl. No. 12/024,811, filed Feb. 1, 2008; Inventors: Anthony Diodati et al.

Non-Final Office Action dated Apr. 29, 2010 from U.S. Appl. No. 12/024,811, 25 pages.

\* cited by examiner

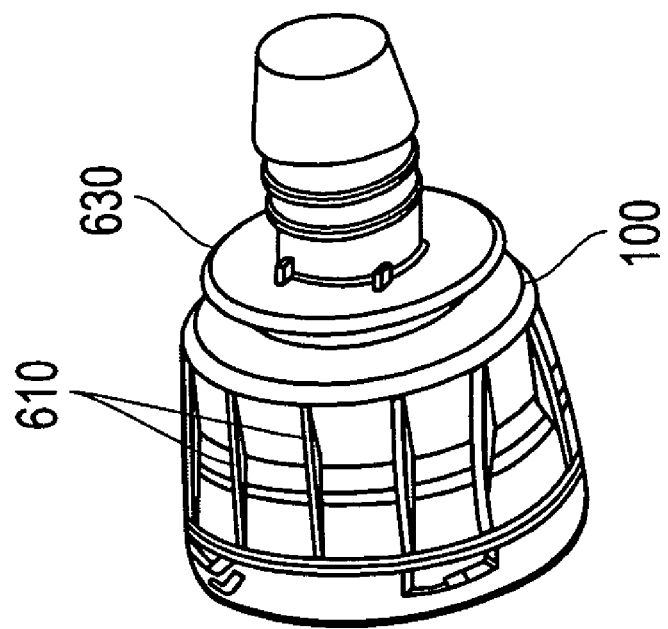
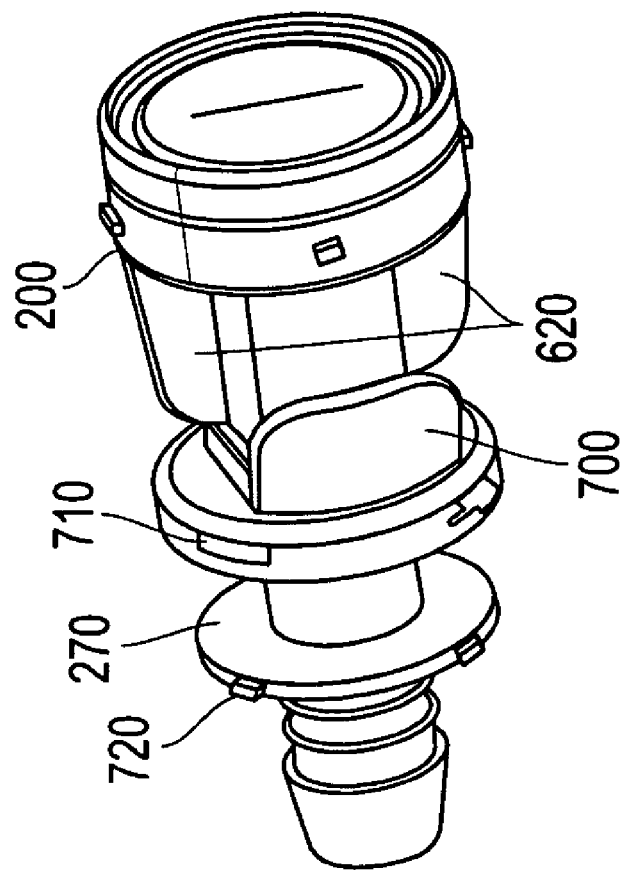
FIG. 6

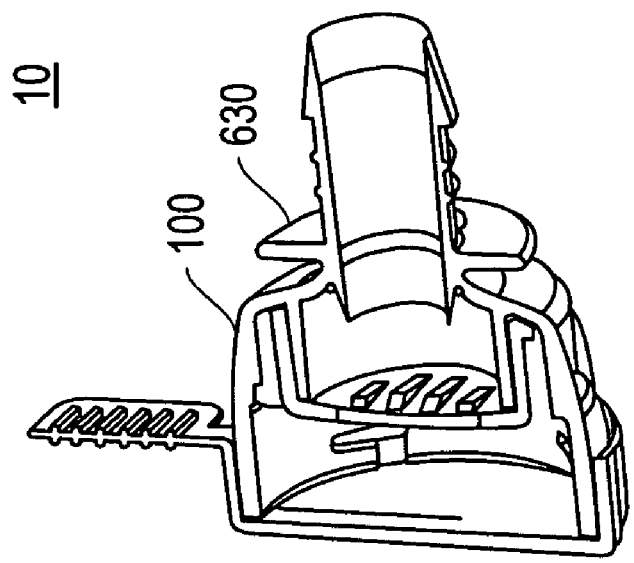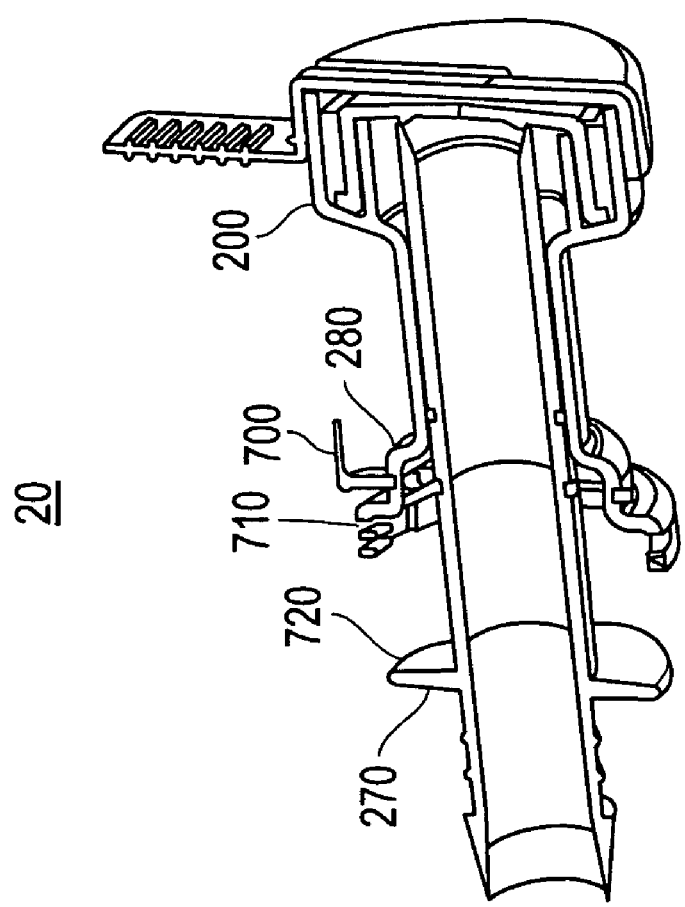
FIG. 7

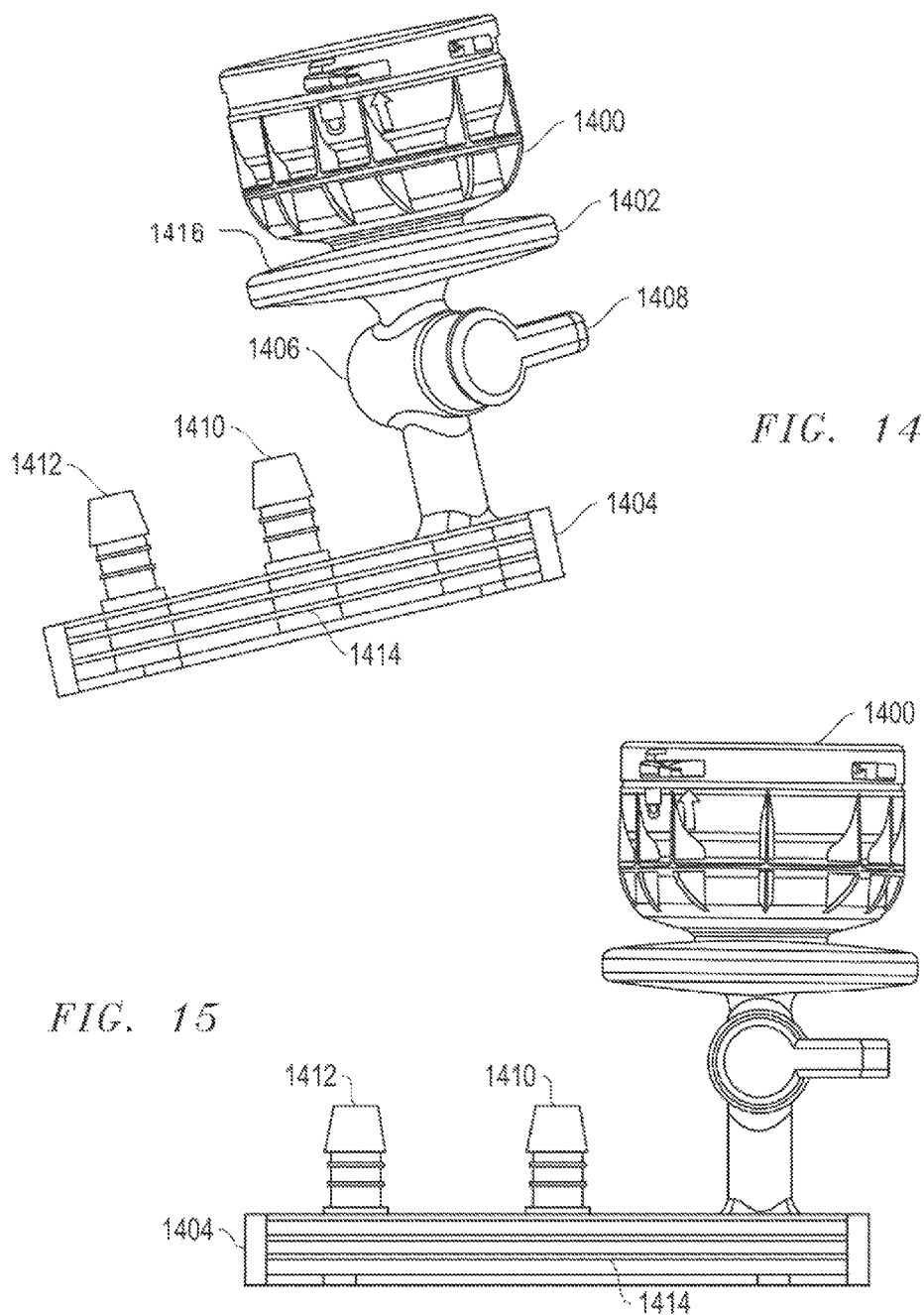

CONNECTOR ASSEMBLY

CORRESPONDING APPLICATIONS

The present application claims priority to U.S. Provisional Patent Application No. 61/039,311, filed Mar. 25, 2008, entitled "CONNECTOR ASSEMBLY," naming inventors Anthony Diodati, Albert A. Werth, Clemens E. Zoellner, Anthony Pagliaro, and Jeffrey Chase, which application is incorporated by reference herein in its entirety.

The present application claims priority to and is a continuation-in-part of U.S. patent application Ser. No. 12/024,811, filed Feb. 1, 2008, entitled "CONNECTOR ASSEMBLY," naming inventors Anthony Diodati, Albert A. Werth, Clemens E. Zoellner, Anthony Pagliaro, and Jeffrey Chase, which claims priority to U.S. Provisional Patent Application No. 60/887,751, filed Feb. 1, 2007, entitled "CONNECTOR ASSEMBLY," naming inventor Anthony Diodati, Albert A. Werth, Clemens E. Zoellner, Anthony Pagliaro, and Jeffrey Chase, each of which is incorporated by reference herein in its entirety.

FIELD OF THE DISCLOSURE

This disclosure, in general, relates to a connector assembly. More particularly, the disclosure relates to a sterile connector assembly.

BACKGROUND

Large-scale production of pharmaceuticals, fluids for use in medical applications, and food grade products relies on maintenance of sanitary environments. Exposure of such products to bacteria or contaminants results in a reduced quality and, in some cases, toxic byproducts. As such, food and medical product manufacturers attempt to reduce points of contamination and have turned to sanitary hoses and connectors as part of an effort to maintain a sanitary environment.

In part, manufacturers have turned to connectors with seals. However, typical seals on such connectors are removed just prior to use, resulting in possible exposure of the fluid to the ambient environment. As such, improved connectors would be desirable.

BRIEF DESCRIPTION OF THE DRAWINGS

The present disclosure may be better understood, and its numerous features and advantages made apparent to those skilled in the art by referencing the accompanying drawings.

FIGS. 1, 2, 3, 4, 5, 6 and 7 include illustrations of exemplary connectors.

FIG. 14, FIG. 15, and FIG. 16 include illustrations of exemplary connectors including a fitment.

The use of the same reference symbols in different drawings indicates similar or identical items.

DETAILED DESCRIPTION OF THE DRAWINGS

Figure 1:
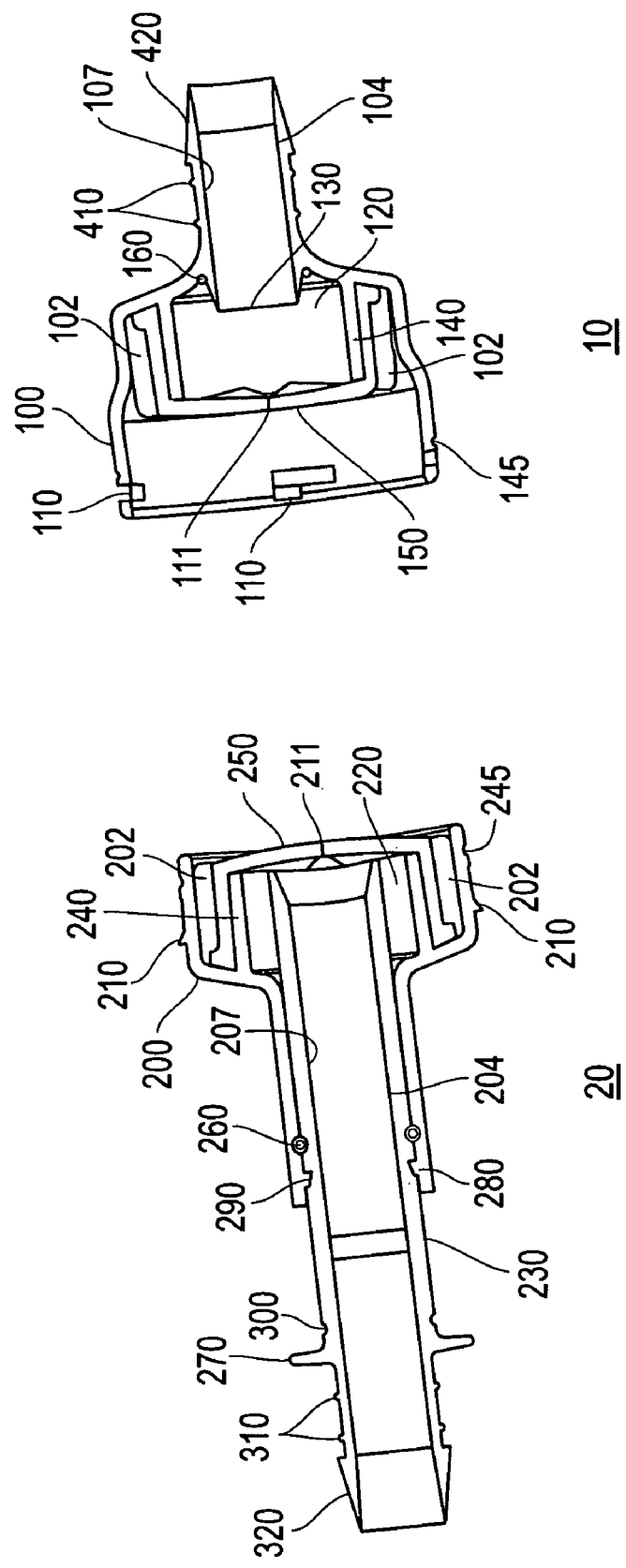

In an exemplary embodiment, a connector includes mating connectors that can be coupled together and to various fluid conduit systems to provide a fluid path between the fluid systems. The connector assembly provides a sterile environment for fluid to flow between containers or conduits and prevents contaminants from entering the fluid path.

In an embodiment illustrated in FIGS. 1, 2, 3, 4, and 5 the connector assembly includes two connectors 10 and 20. The first connector 10 includes a housing 100 that defines a seal structure 130 and a coupling 420. The second connector 20 includes a housing 200 surrounding a stem 230. In an example, the stem 230 is configured to move axially relative to the housing 200. The stem 230 may include a coupling 320. When the first connector 10 and the second connector 20 are coupled, the first and second housings (100 and 200) are configured to lock together and the stem 230 is configured to engage the seal structure 130 to define a fluid passage through the coupling assembly. For directional orientation, each connector (10 and 20) and their associated housings (100 and 200) have a proximal end illustrated nearest the opposing connector and a distal end illustrated furthest from the opposing connector. The proximal ends of the first housing 100 and second housing 200 are dimensioned to matingly engage. In an embodiment, the first housing 100 has an inside diameter and the second housing 200 has an outside diameter wherein the inside diameter of the first housing 100 is greater than the outside diameter of the second housing 200 to provide a frictional fit. In an alternative embodiment, the first housing 100 has an outside diameter and the second housing 200 has an inside diameter wherein the inside diameter of the second housing 200 is greater than the outside diameter of the first housing 100 to provide a frictional fit.

In an embodiment, the first housing 100 and the second housing 200 may include an interlocking mechanism adapted to interlock the first housing 100 in a predetermined relationship with the second housing 200. In an example, the interlocking mechanism may have any suitable configuration to prevent the axial movement of first housing 100 relative to the second housing 200 when they are matingly engaged. The interlocking mechanism may also be configured to prevent rotational movement of first housing 100 relative to the second housing 200 when they are matingly engaged. Exemplary interlocking mechanisms include threaded connections or tab and groove connections. In an example illustrated in FIG. 1, the first housing 100 includes an inner sidewall with a groove 110 along at least a portion of the circumference of the sidewall. One or more grooves 110 may extend along the inner sidewall. The opposing second housing 200 includes an outer diameter. The outer diameter of the second housing 200 includes one or more tabs 210 that extend beyond the periphery of the outside diameter. Hence, when the second housing 200 and first housing 100 are matingly engaged, the tabs 210 of the second housing 200 engage the grooves 110 of the first housing 100 to interlock the housings 100, 200. For example, tabs 210 are configured to bend with the frictional force of the sidewall of first housing 100 and grooves 110. In an exemplary embodiment, the grooves 110 are configured such that first housing 100 and second housing 200 are rotated to engage the tabs 210 with the grooves 110 and lock the housings 100 and 200. For example, the groove 110 may be configured in an "L" shape to first proximally and axially guide the tab 210 and next rotationally guide the tab with first housing 100. In an embodiment, the interlocking device is arranged to irreversibly lock when engaged, i.e., the unlocking would result in damage to the housing (100 or 200). In an additional embodiment, an indicator may be disposed on the housing (100 or 200) to indicator alignment and locking of the housings. For example, an indicator may be etched on to the housing (100 or 200), such as an arrow or line etched onto the outer surface of the first housing 100 and an arrow or line etched onto the outer surface of the second housing 200 that align when the housings 100 and 200 are interlocked together.

In an embodiment, the first housing 100 includes a valve support structure 140 that defines a first aperture 120 or internal chamber with an open proximal end. Further, the second housing 200 includes a valve support structure 240 that defines a second aperture 220 or internal chamber with an open proximal end. Typically, the first aperture 120 and the second aperture 220 are configured to align, such as aligning in a concentric fashion along an axis, when the first housing 100 is coupled to the second housing 200. As illustrated, the valve support structures 140 and 240 are integrally formed within the housings 100 and 200, respectively. Alternatively, the valve support structures 140 and 240 may be formed as separate pieces and fixed within the housings 100 and 200, respectively.

In an embodiment, the stem 230 and the seal structure 130 matingly engage with a frictional fit. Alternatively, the connector 10 may include an axially movable stem and the connector 20 may include a seal structure 130. In a further example, both connectors 10 and 20 may include axially movable stems. In a particular embodiment, the stem 230 and seal structure 130, when engaged, define a generally hollow body having an interior surface (107, 207), defining a lumen 109 for fluid flow therethrough to connect the distal ends of connectors 10 and 20, such as a fluid passage between the couplings 420 and 320.

In an exemplary embodiment, a valve 150 seals the open proximal end of the first aperture 120 defined by the first housing 100. The valve 150 is affixed to prevent inadvertent displacement of the valve 150 and exposure of the first aperture 120 to the ambient environment. For example, the valve 150 may be attached to the valve support structure 140 defining the first aperture 120 through any suitable technique to physically or chemically attach the valve 150. In an exemplary embodiment, the valve 150 is permanently affixed to the valve support structure 140. In an embodiment, the valve 150 is permanent affixed with a valve retainer 102. The valve retainer 102 may be disposed between the valve 150 and the inside diameter of the housing 100 in any suitable configuration to permanently affix the valve 150 to the valve support structure 140. For instance, the valve retainer 102 may be dimensioned to frictionally fit the valve 150 to the valve support structure 140.

In addition, a valve 250 may seal the open proximal end of the second aperture 220 in the second housing 200. The valve 250 may be affixed to prevent inadvertent displacement of the valve 250 and exposure of the second aperture 220 to the ambient environment. The valve 250 may be attached to the valve support structure 240 defining the second aperture 220 through any suitable technique to physically or chemically attach valve 250. The valve 250 may be permanently affixed to the valve support structure 240. In an embodiment, the valve 250 is permanent affixed with a valve retainer 202. The valve retainer 202 may be disposed between the valve 250 and the inside diameter of the housing 200 in any suitable configuration to permanently affix the valve 250 to the valve support structure 240. For instance, the valve retainer 202 may be dimensioned to frictionally fit the valve 250 to the valve support structure 240.

Figure 2:
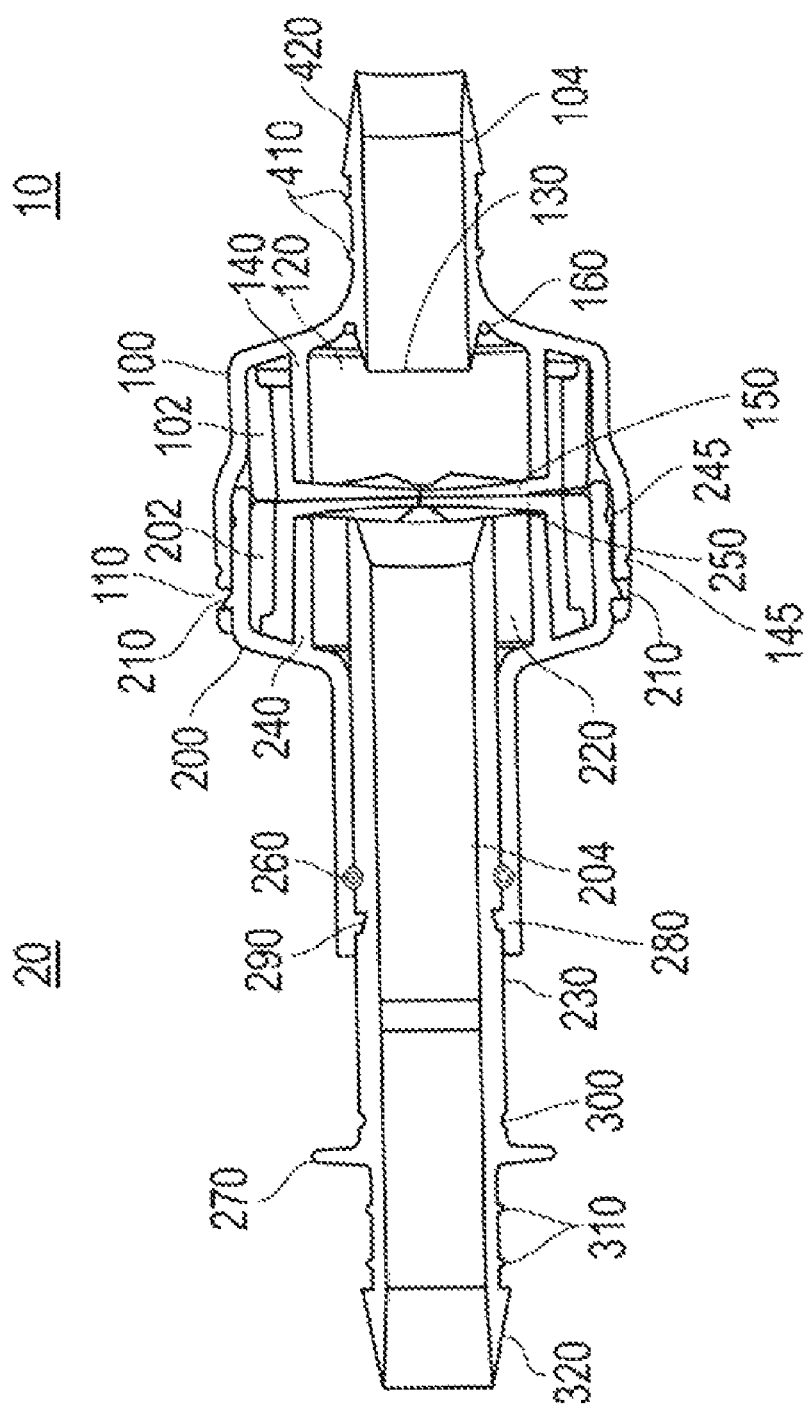

In an embodiment, the valve 150 is configured to align with valve 250. For example, the housings 100 and 200 may be dimensioned such that when the first housing 100 and the second housing 200 matingly engage, valve 150 aligns with and contacts valve 250, as illustrated in FIG. 2. In particular, valve 150 may include a slit 111 and valve 250 may include a slit 211, which are aligned when the housings 100 and 200 are matingly engaged. In an exemplary embodiment, valve 150 engages or may adhere to valve 250. The valves 150 and 250 may have a dome-shaped configuration where the convex portion extends toward the proximal end of the second aperture 220 and the first aperture 120, respectively, to facilitate face-to-face engagement of the valves 150 and 250.

In an embodiment, the stem 230 is movably housed in the second housing 200. For example, the stem 230 is dimensioned to move axially within the second housing 200 and proximally to engage the seal structure 130 in first housing 100. In an example, the distal end of the stem 230 includes a flange 270 on the outside diameter of the stem 230. Typically, once the valves 150 and 250 are aligned, the stem 230 is engaged to move axially and proximally through the valve 250 and the valve 150 to fold both valves 150 and 250 in the direction of the movement of the stem 230 and to the outside diameter of the stem 230 until the stem 230 engages the seal structure 130. In an exemplary embodiment, the stem 230 engages a seal 160, such as an o-ring, on the proximal end of the seal structure 130 to provide a tight frictional fit.

Figure 17:
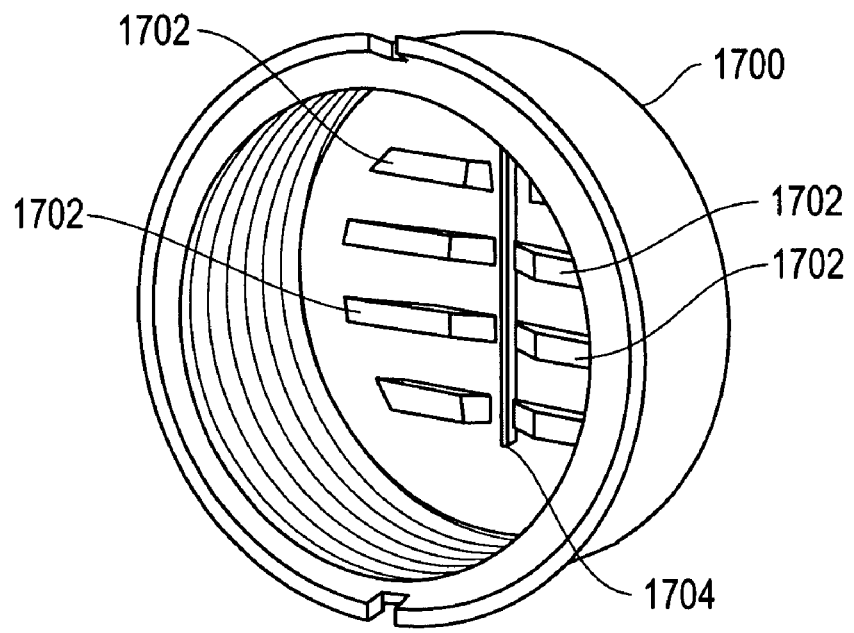
FIG. 17 and FIG. 18 include illustrations of exemplary valves.

In an example, the valve 150 or the valve 250 may be configured with a slit and support ridges. As illustrated at FIG. 17, a valve 1700 includes ridges 1702 and a slit 1704. The ridges 1702 may provide support for the material of the valve and may provide the valve 1700 with a convex outer surface that presses against an opposing valve when respective connectors are interconnected. In another example, the ridges 1702, when disposed on the connector 20 within the aperture 220, contact the leading edge of the stem 230 as the stem 230 moves through the valve 250 causing the slit 1704 to open without contact by the stem 230. In this manner, the stem 230 does not contact the slit 1704 and does not contact the outer surface of the valve 250 or 150, preventing contamination.

The slit 1704 may provide a passageway for the stem. As illustrated in FIG. 17, the slit is cut perpendicular to the ridges 1702. Alternatively, the slit 1704 may be cut as a cross into the valve 1700. In another example, two or more slits that intersect at a center point may be cut into the valve 1700. In such an example, ridges may be disposed to project toward the center point.

Figure 18:
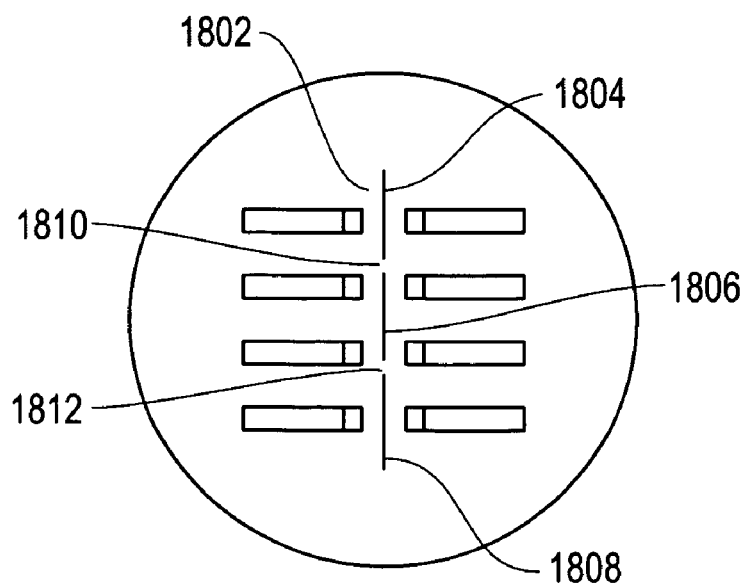

In an embodiment, the slit 1704 is cut into the valve 1700 and partially re-knitted through heat or radiation treatment. In an alternative embodiment illustrated in FIG. 18, the slit may be cut in portions separated by an uncut portion or web structure. As illustrated in FIG. 18, the slit 1802 has three portions (1804, 1806 and 1808). The slit portions (1804, 1806, and 1808) are separated by web structures 1810 and 1812. In an example, the web structures 1810 and 1812 have a thickness parallel to the longitudinal axis of the slit 1802 in a range of ½0th to ¼0th the length of the longest slit portion (1804, 1806, and 1808) along the longitudinal axis. For example, when the longest slit portion is approximately 300 mils, the thickness of the web structure may be between 7.5 mils and 15 mils, such as approximately 10 mils. When a stem is pushed through the slit 1802, the web structures 1810 and 1812 extend and break. As such, the web structures 1810 and 1812 maintain the slit 1802 in a closed position during transport and handling, meeting sterility standards, while allowing the stem to be pushed through the slit 1802 for deployment without excessive force exerted by a user. When two web structures are used as part of the slit, the valve is referred to as a double web valve.

In a further embodiment, the stem 230 may include a locking mechanism. The locking mechanism may be of a configuration that restricts the axial retreat of the stem 230 within the second housing 200. The second housing 200 is typically dimensioned to allow axial advancement of the stem 230 and maintain a tight fit with seal structure 130. In an exemplary embodiment, once seal 160 is engaged with stem 230, the locking mechanism may prevent axial movement of the stem 230 in the distal direction relative to the second housing 200. For example, a locking tab 290 may be located on the inside diameter of the distal end of the housing 200. In an example, the locking tab 290 may be a radially projecting fin. Further, one or more grooves 280, 300 may be located on the outside diameter of stem 230 and may be configured to engage the locking tab 290. The first groove 280 may be configured along the central axis of stem 230 to prevent movement of the stem 230 in the distal direction relative to the housing 200 and accidental exposure of the aperture 220 to the environment prior to engaging first housing 100. Once the first housing 100 and the second housing 200 are engaged, the flange 270 is moved proximally until the second groove 300 is engaged with the locking tab 290. The second groove 300 may be configured along the distal axis of the stem 230 to prevent further axial movement once the stem 230 is engaged with the seal 160, such as to prevent the stem 230 from disengaging the seal 160. In an embodiment, the locking mechanism irreversibly locks when engaged.

The stem 230 may include an interlocking mechanism that is configured to pass through the housing 200 to engage stem 230. As illustrated in the embodiments of FIGS. 6, 7, 8, 9, and 10 the interlocking mechanism includes a clip 700. Clip 700 may be shaped in a horseshoe configuration with a forked end 810 and a closed end 820. The closed end 820 is typically configured for the user to engage the interlocking mechanism and may be dimensioned with a flat face. In an embodiment, the interior of forked end 810 includes elongated tabs 830. The forked end 810 may further include hooks 840. The elongated tabs 830 can engage the first groove 280 located on the outside diameter of the stem 230. Once the first housing 100 and the second housing 200 are engaged, the closed end 820 is pushed toward the housing 200 to disengage the elongated tabs 830 from the first groove 280. The hooks 840 may be dimensioned to engage the outside diameter of the housing 200 to lock the clip 700 in an open position. The clip 700 is dimensioned to allow proximal movement of the stem 230 once the hooks 840 engage the outside diameter of the housing 200. In an embodiment, the locking mechanism irreversibly locks when engaged.

Figure 12:
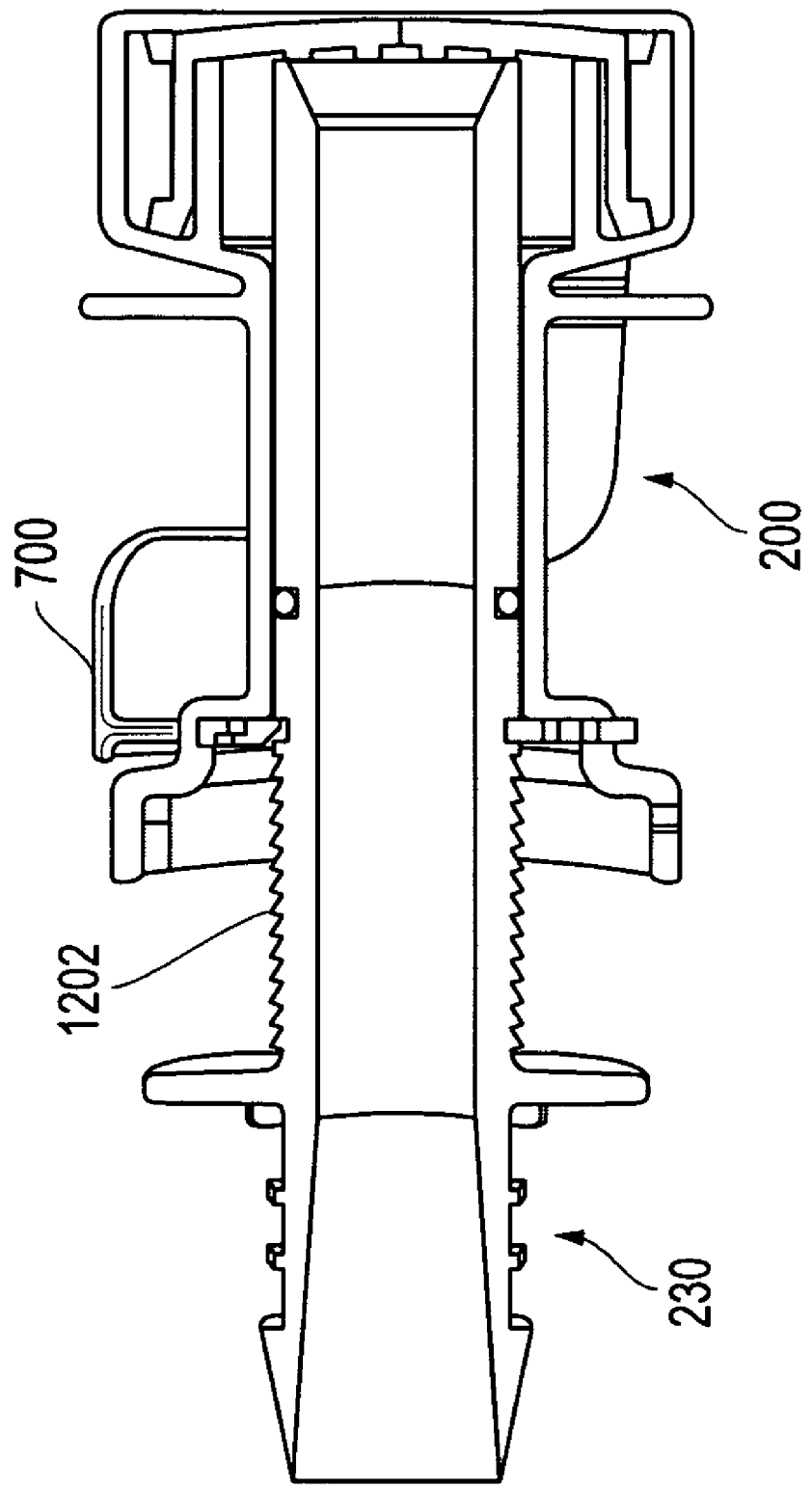
FIG. 12 includes an illustration of an exemplary connector.

In a further example, the stem 230 may include a set of adjacent ridges 1202, as illustrated in FIG. 12. For example, the adjacent ridges 1202 may be concentric ridges to engage the housing 200 or the clip 700. In particular, the adjacent ridges 1202 and the housing 200 or the clip 700 engage to permit the stem 230 to ratchet forward, preventing backward or reverse movement of the stem 230.

In a further embodiment, one or more locking tabs 720 may be configured along the outside diameter of the flange 270. The distal end of the housing 200 may be configured to engage the flange 270 and the locking tab 720. For instance, the inside diameter of the distal end of the housing 200 may be greater than the outside diameter of the flange 270 to enable the flange 270 to matingly engage the distal end of the housing 200. Further, the distal end of the housing 200 may include complementary grooves 710 to matingly engage the tabs 720 of the flange 270 to interlock the flange 270 and the housing 200. For example, the tabs 720 are configured to bend with the frictional force of the sidewall of the second housing 200 and the grooves 710. In an exemplary embodiment, the grooves 710 are configured such that the flange 270 and the second housing 200 are rotated to engage the tabs 720 with the grooves 710 and lock the flange 270 and the housing 200. For example, the groove 710 may be configured in an "L" shape to first proximally and axially guide the tab 720 and next rotationally guide the tab with the second housing 200. The groove 710 and the tab 720 may be configured to prevent further axial movement once the stem 230 is engaged with the seal 160, such as to prevent the stem 230 from disengaging the seal 160. In an embodiment, the locking mechanism irreversibly locks when engaged. In a further embodiment, the stem 230 may include additional wings extending radially outwardly that permit a user to rotate the stem 230 to engage the tabs 720 with the grooves 710. In another example, the housing 200 may include an indicator, such as an etched arrow or line, that aligns with an indicator on the stem 230 or the flange 270 to indicate interlocking of the housing 200 and the stem 230.

Figure 19:
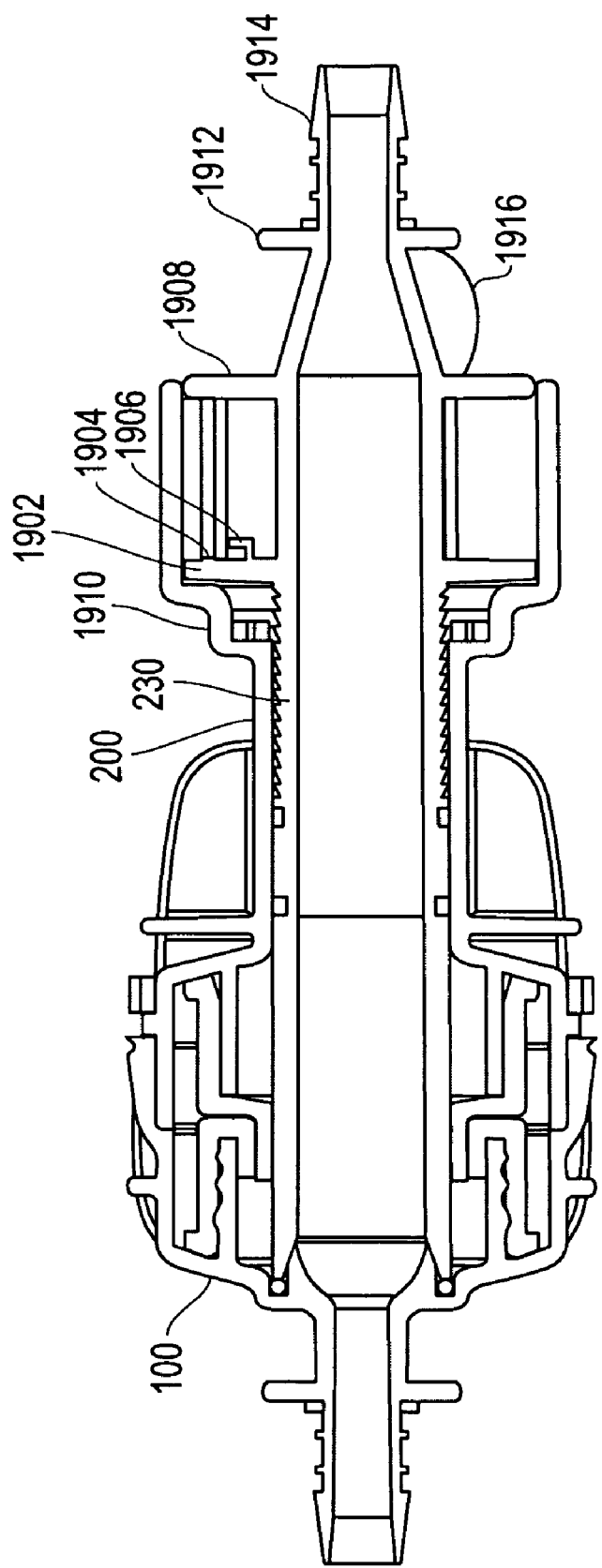
FIG. 19 includes an illustration of an exemplary connector.

In another embodiment illustrated in FIG. 19, the stem 230 may include a first flange 1902 that includes tabs 1904 to engage the housing 200 at grooves 1906. In addition, the stem may include a second flange 1908 that, when the tabs 1904 are engaged and locked with grooves 1906, aligns with the flared end of the housing 200. In such a manner, a user may apply force to the second flange 1908 to assist with insertion of the stem 230 to engage the opposite connector. For example, the user may use a shoulder 1910 of the housing and the second flange 1908 as leverage against each other to move the stem 230. In addition, the stem 230 may include a third flange 1912 as a tube stop when a tube is inserted onto the connector 1914. Further, the stem 230 may include a wing 1916 to assist with rotating the tabs 1904 into interlocking position with the grooves 1906.

Returning to FIGS. 1-5, to provide a conduit for fluid flow, the stem 230 and the seal structure 130 may slidingly engage after pushing open the valves 150 and 250. In an embodiment, the engaged valves 150 and 250 are configured to fold toward the distal end of first housing 100 along the outside diameter of the second stem 230, for example, in the direction of the movement of the stem 230. The valves 150 and 250 and the apertures 120 and 220 are configured such that fluid flow is prevented from contacting the valves 150 and 250 when the stem 230 is in contact with the seal structure 130, maintaining a sterile environment. In addition, the valve 250 may include ridges disposed on the aperture 220 side of the valve 250 which contact the stem 230 as it passes through a slit in the valve and prevent the stem 230, particularly the seal surface 231 and peak 232 of the stem 230, from contacting the slit and the outside surface of the valve 250.

The integrity of the sterile environment may be maintained through the stem 230 contacting the seal structure 130, while not being exposed to the environment beyond the sealed apertures 120 and 220. In particular, the stem 230 is configured to move through the valves 150 and 250 without contacting an outside surface of the valves 150 and 250. In an embodiment, the connector 10 includes the seal structure 130 and a seal 160 around the proximal end of the seal structure 130. The seal structure 130 is configured to engage the proximal end of stem 230 after the first and second housings 100 and 200 engage. For instance, the proximal end of the stem 230 is dimensioned to form a tight frictional fit between the seal structure 130 and the stem 230 when the stem 230 is matingly engaged with seal structure 130 and engages seal 160. In an example, the seal 160 may be continuous and may completely engage the proximal end of the stem 230. For example, the seal 160 may be an O-ring.

In a particular example, the stem 230 does not extend into a lumen defined by the inner surface 107 of the housing 100 or the liner 104. Instead, the stem 230 engages an outer seal surface 131 of the seal structure 130. In particular, the seal structure 130 may be formed as a bevel, wherein the peak 132 of the bevel aligns with the surface of the lumen and the seal surface 131 is formed as the bevel slopes from the peak 132. Thus, the seal surface 131 faces radially outwardly and forms a separate surface from an inner surface 107 of the seal structure and fluid conduit. Complementarily, the stem 230 includes an inner bevel wherein the peak 232 is formed closer to an outside surface of the stem 230 and a seal surface 231 is formed as the bevel slopes toward an inner surface 207 of the stem 230. Thus, the seal surface 231 faces radially inwardly and forms a separate surface from the inner surface 207 of the stem 230 and an outer surface of the stem 230.

When the connectors 10 and 20 are connected and the stem 230 engages with the seal structure 130, a smooth fluid pathway 109 is formed. In particular, the interconnection between the stem 230 and the seal structure 130 provides a fluid pathway 109 that is smooth, and varies by less than 5% of the diameter of the fluid pathway 109 at the location of the interconnection of the seal structure 130 and the stem 230, such as less than 1%, less than 0.5%, or even less than 0.2% of the diameter of the fluid pathway 109. Such an interconnection between the stem 230 and the seal structure 130 provides a low pressure-drop pathway and limits space for growth of biological contaminants. Further, such an interconnection is particularly useful when the connectors 10 and 20 are configured for fluid to flow through connector 10 into connector 20.

In an embodiment, the stem 230 is surrounded by the housing 200. The stem 230 is dimensioned to form a tight frictional fit between the outside diameter and distal end of the stem 230 and the distal end of the housing 200. In addition, a seal 260 is located between the housing 200 and the stem 230. For example, the seal 260 may continuously surround the circumference of the stem 230. In an example, the seal 260 may be disposed in a groove in the outside diameter of the stem 230. Alternatively, the seal 260 may be disposed in a groove along an inside surface of the distal end of the housing 200. In an example, the seal 260 may be an O-ring. In a particular embodiment, the seal 260 isolates the volume between the stem 230 and the interior, distal end of housing 200 to isolate the second aperture 220 from the ambient environment and allow the stem 230 to move axially.

Typically, the valves 150 and 250 and the seals 160 and 260 may be formed of any suitable material, which precludes the passage of contaminants. In an embodiment, the valves 150 and 250 and the seals 160 and 260 may be made of any material approved by the FDA for fluid transport. In an exemplary embodiment, the valves 150 and 250 and the seals 160 and 260 may be formed of a polymeric material. An example polymeric material includes an elastomer, such as a silicone elastomer, thermoplastic elastomer, thermoplastic vulcanizate, or polymer containing ethylene propylene diene monomer. The valves 150 and 250 and the seals 160 and 260 may also be treated with an antibacterial compound or contain an antibacterial layer. In a further example, the polymeric material may include an inhibitor to prevent reknitting of the slit, such as a phenyl silicone or fluorosilicone.

Figure 5:
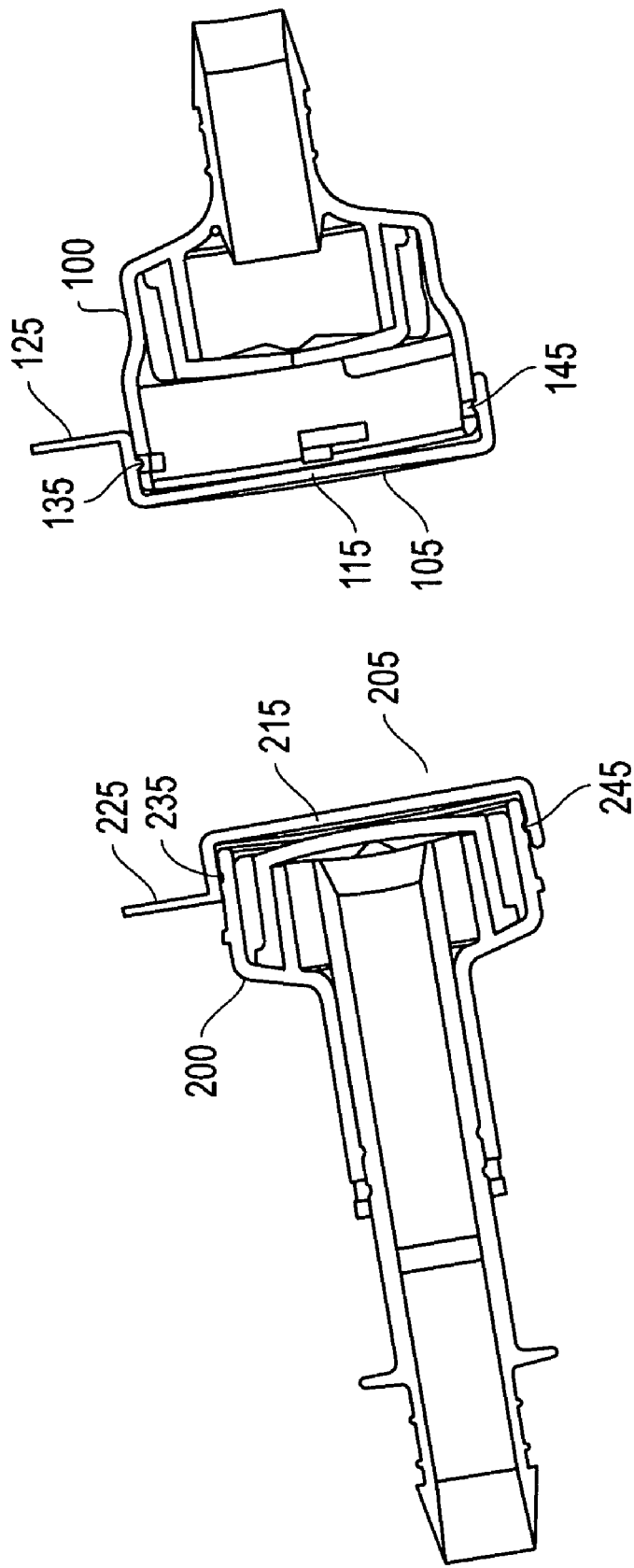

In an embodiment, the proximal end of the housings 100 and 200 may include a cap (105 or 205, respectively) to maintain a sterile environment within the housing as well as protect the valves 150 and 250 from environmental contaminants, as illustrated in FIG. 5. Typically, the caps 105 and 205 may be easily removed prior to coupling the housings 100 and 200. As illustrated in FIG. 5, the caps 105 and 205 may include a cover 115 and 215 and a plurality of ribs 135 and 235. Typically, the proximal ends of the housings 100 and 200 include a sidewall on the outside diameter of the housings 100 and 200 with an annular groove 145 and 245. When the caps 105 and 205 are mounted to the proximal end of the housings 100 and 200, the ribs 135 and 235 engage the annular grooves 145 and 245 to securely hold the caps 105 and 205. In an embodiment, the caps 105 and 205 are dimensioned to fully contain the interior of the housings 100 and 200. The sidewalls of the housings 100 and 200 are dimensioned so that the caps 105 and 205 do not engage the valves 150 and 250. The caps 105 and 205 may further include a tab 125 and 225 attached to the covers 115 and 215 so the caps 105 and 205 can be easily removed.

Figure 13:
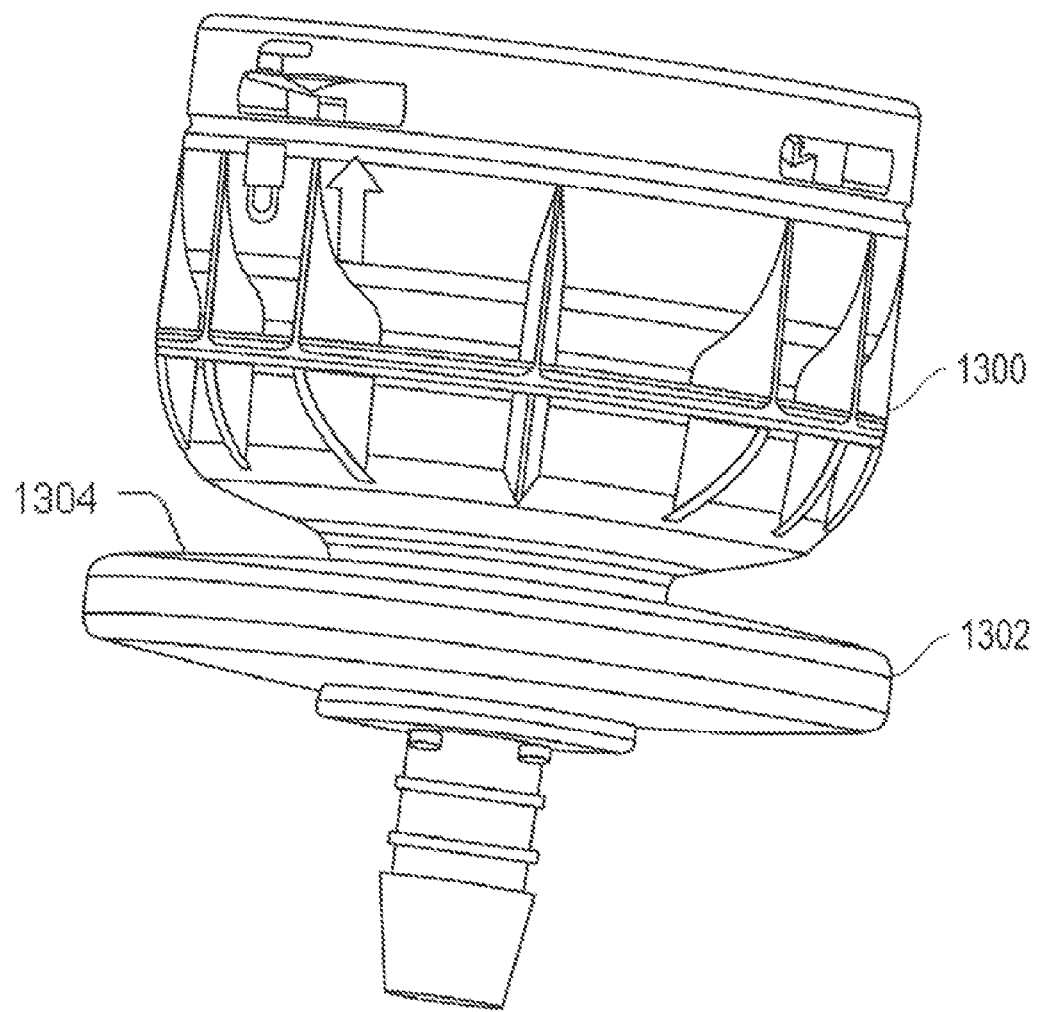
FIG. 13 includes an illustration of an exemplary connector portion including an integral filter.

In an embodiment, the housing 100 or 200 may be configured to facilitate gripping of the housing by the user. Particularly, the housing 100 or 200 may be configured so the user can easily engage the housing 100 or 200. For instance, the outside surface of the housing 100 or 200 may have roughened, textured, or raised features. As illustrated in FIG. 6, the housing 100 may contain a plurality of ridges 610 along at least a portion of the outside surface of the housing 100. The housing 100 may also contain a flange 630. In an alternative embodiment, the flange 630 of the housing 100 may incorporate a filter as described below in relation to FIG. 13. In another exemplary embodiment, the housing 200 includes a plurality of wings 620 along the outside surface of the housing 200. The wings 620 may assist a user when twisting the assembly to interlock the two connectors. As illustrated in FIG. 19, the stem 230 may also include one or more wings 1916 to assist with interlocking the housing 200 and the stem 230 when the stem is extended.

The connector assembly may be made of any material that is compatible with the nature of the particular fluid or sterilization technique utilized. In an embodiment, at least a portion of the connector assembly, such as the housings 100 and 200 and the caps 105 and 205 are made of any material approved by the FDA for fluid transport, such as USP ADCF (animal derived component free) materials and USP Class VI/ADCF materials. In an exemplary embodiment, the materials may be polyvinylidene fluoride, polypropylene, or a combination thereof. Further, the housing may include independent, multiple components or continuous, integral components.

In an exemplary embodiment, the stem 230 has an interior surface and an exterior surface. Further, the housing 100 defining the seal structure 130 may also have an interior and an exterior surface. The interior surface, for example, defines a lumen for fluid flow therethrough. In general, the interior surface 107 has an initial roughness (Ra) not greater than 50 microns, such as not greater than about 10 microns, or not greater than about 1 micron, or even not greater than 500 nm. An exemplary polymer for use in the housings, stems, seals, and other components includes a polyolefin. In an example, the polyolefin includes polyethylene or polypropylene. In particular, the polyolefin may include halogenated polyolefin. For example, the halogenated polyolefin may include polyvinyl chloride (PVC), polyvinyl fluoride (PVF), polyvinylidene fluoride (PVDF), polyvinylidene chloride (PVDC), polycholorotrifluoroethylene (PCTFE), polytetrafluoroethylene (PTFE), or blends or copolymers thereof. In a particular embodiment, the fluid pathway in the housings and stem may include a liner 104 or 204. In an example, the liner 104, 204 is formed of a perfluoronated polymer, such as PTFE. In a particular embodiment, a fluoropolymer may be selected from those sold under the Chemfluor® trademark, available from Saint Gobain Performance Plastics Corporation. In another example, the material may include silicone. In a further example, the material may be elastomeric.

The distal end of each housing 100 and 200 may be configured to engage a fluid system, such as a section of tubing. For example, the outside diameter of the distal end of the stem 230 the housing 100 opposite the seal structure 130 may include at least one annular rib 310, 410 or barb to engage a section of tubing. The distal end of the stem 230 and the housing 100 may further include a tapered outside diameter to define couplings 320, 420 to provide axial guidance for tubing and a tight frictional fit to provide a seal between the inside diameter of the tubing and the outside diameter of the distal end of the stem 230 and of the housing 100. Alternatively, the stem 230 and the housing 100 may be configured with couplings of other types, such as those coupling configurations known in the industry. In an embodiment, the distal end of the first housing 100 and the stem 230 are configured with an outside diameter of about ¼ inch, about ⅜ inch, and about ½ inch.

Figure 11:
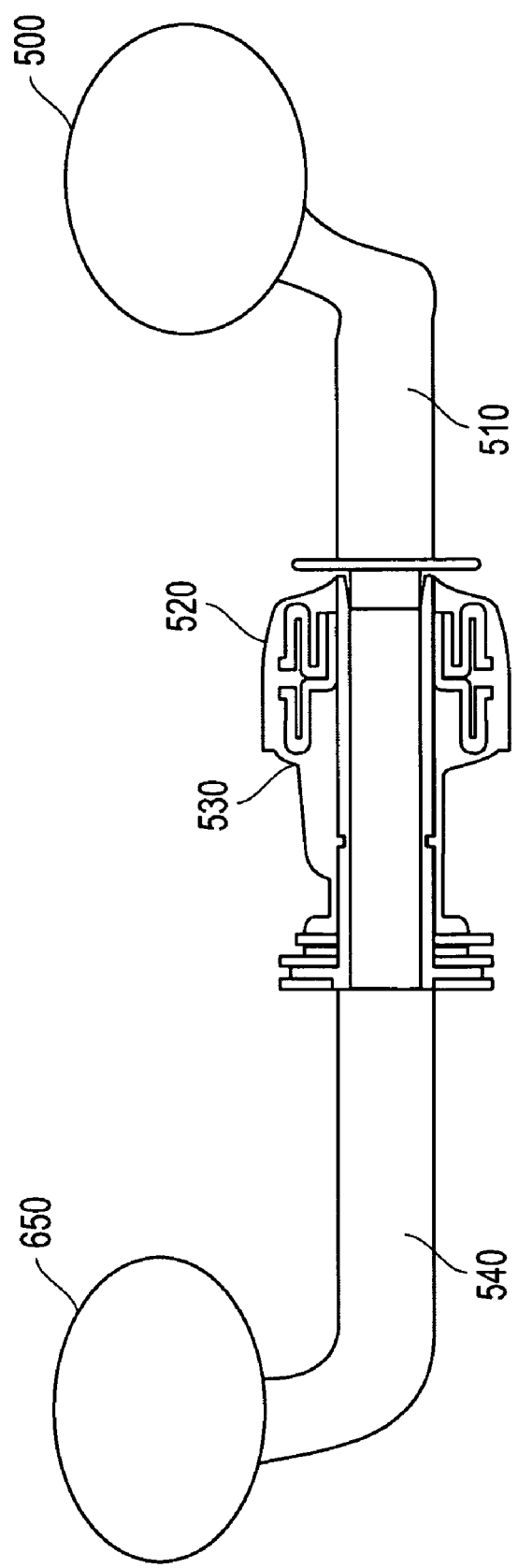
FIG. 11 includes an illustration of an exemplary assembly including an exemplary connector.

Each connector may be attached to or may be formed as part of any suitable fluid container or conduit, for example, a section of tubing, an inlet or outlet of a housing, such as a filter housing or drip chamber housing, or a flexible bag such as a blood bag. FIG. 11 includes an illustration of an exemplary fluid system in which a container 500 is fluidically coupled to a container 650 through a tubing 510 coupled to a first connector 520 that is coupled to a second connector 530, which is coupled to a tubing 540 that is coupled to the container 650. In particular, the connector may be suitable for fluid communication where the pressure rating is greater than or equal to about 50 psi or 3.5 bar.

In an exemplary embodiment, the connector assembly is suitable for sterilization. In an embodiment, the connector may be sterilized by radiation sterilization or heat sterilization. In particular, the materials of the connector may be selected based on the anticipated method of sterilization. Particularly, the connector assembly may be configured for sterilization in an autoclave at temperatures of about 134° C. at 17 psi for about 1 hour. Alternatively, the connector assembly may be configured for sterilization by radiation using gamma rays at 25 kGy for 2 doses, or even 50 kGy for one or more doses. Further, the connector assembly may be packaged to maintain sterilization.

Figure 3:
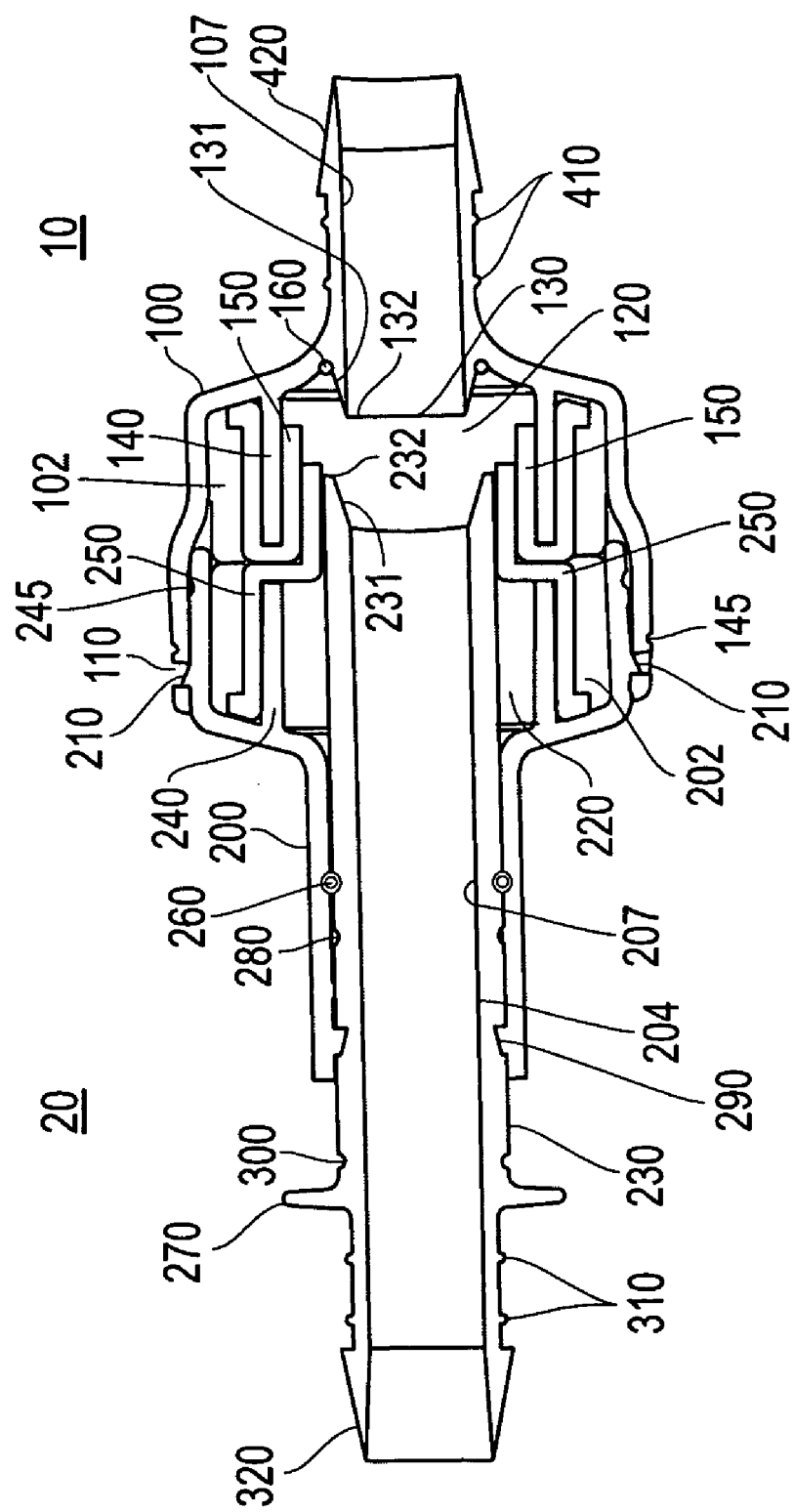
Figure 4:
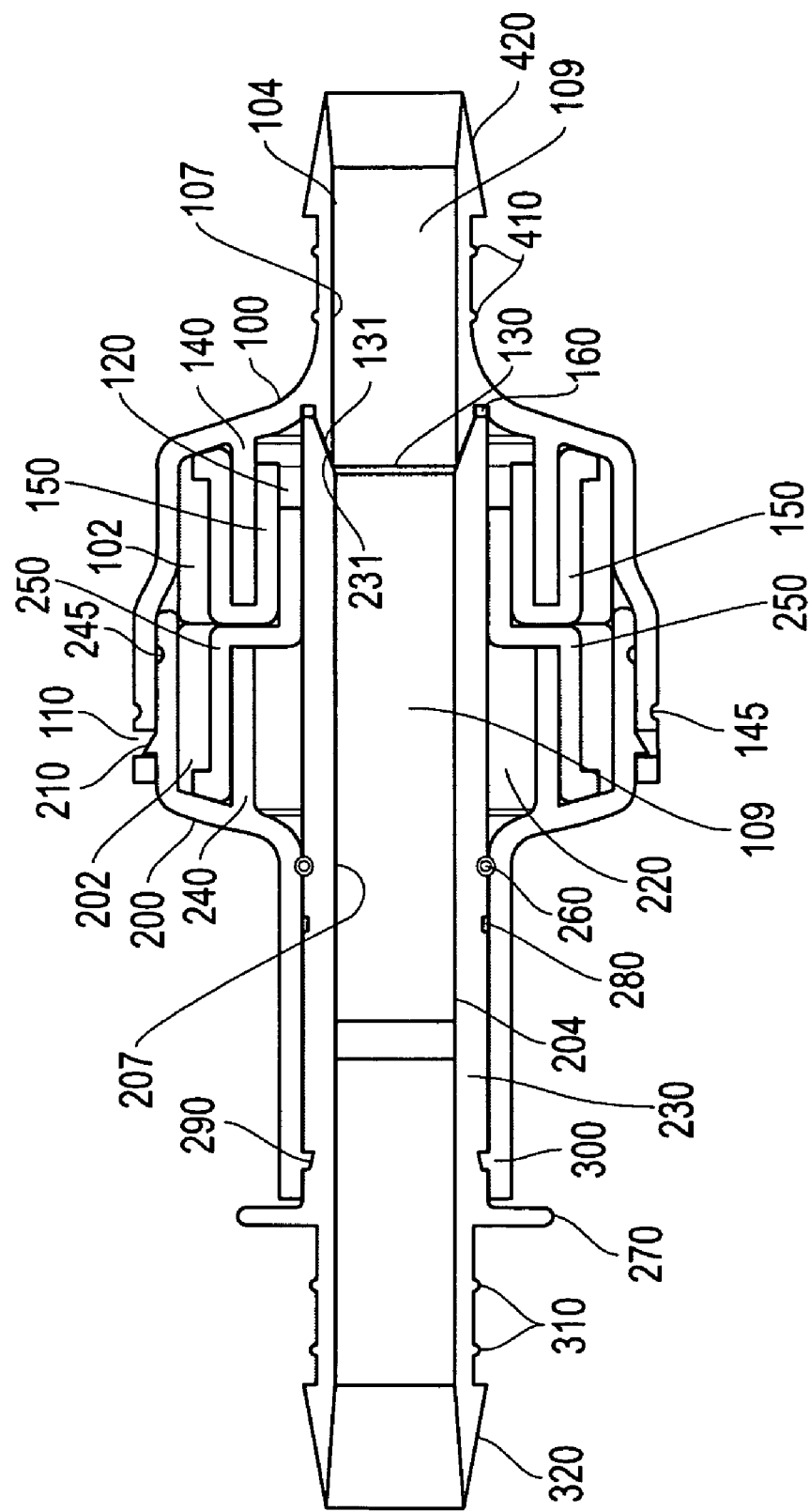

In an exemplary embodiment, operation of the connectors includes removing the caps 105 and 205 from the first housing 100 and the second housing 200, respectively. The operator then matingly engages the first housing 100 and the second housing 200, as illustrated in FIG. 2. The interlocking tab 210 of the second housing 200 engages the groove 110 of the first housing 100 axially and proximally and the housings 100 and 200 are rotated and permanently locked. An indicator may align to confirm interlocking. When the housings 100 and 200 are pushed together, the valves 150 and 250 engage and seal to one another. An operator may push the flange 270 to axially and proximally move the stem 230. The stem 230 may open the path for fluid to flow through by pushing open the valves 150 and 250 in the direction of the movement of the stem 230 and to the outside diameter of the stem 230, as illustrated in FIG. 3. Ridges on the valve 250 may prevent the stem 230 from contacting the slit and outer surfaces of the valves 150 and 250 as the stem 230 pushes through the valves 150 and 250. In addition, the stem 230 may act to stretch and break web structures keeping the slit of the valves 150 and 250 closed. For example, the web structures may hold the slit closed until the stem 230 is pushed through the valves 150 and 250. The flange 270 is pushed until the stem 230 engages the seal 160 of the seal structure 130, the stem 230 is locked into position by the tab 290 and the second groove 300, and the stem 230 is sealed with the seal 260, as illustrated in FIG. 4. Optionally, the stem 230 may include a flange with tabs that interlock with the housing 200 to prevent the stem 230 from loosing contact with the seal 260. The sanitary and sterile connection is complete.

Figure 9:
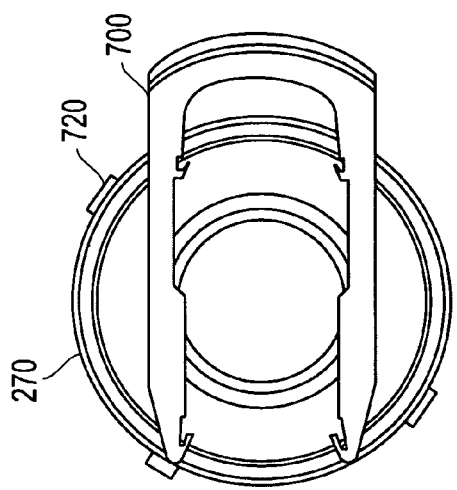
FIGS. 8, 9, and 10 include illustrations of an exemplary interlocking mechanism.
Figure 10:
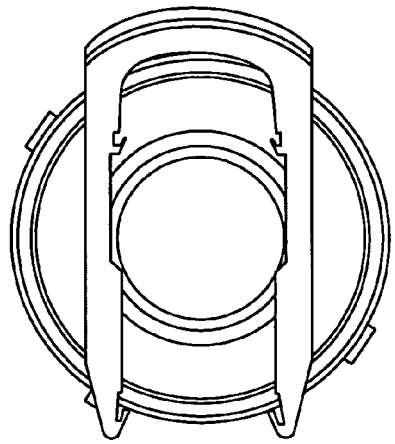
Figure 8:
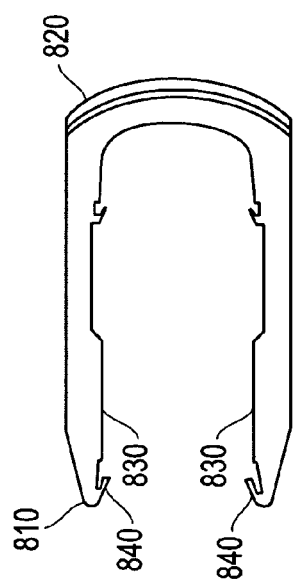

In another exemplary embodiment, operation of the connectors includes removing the caps 105 and 205 from the first housing 100 and the second housing 200, respectively. The operator then matingly engages the first housing 100 and the second housing 200. The interlocking tab 210 of the second housing 200 engages the groove 110 of the first housing 100 axially and proximally, and the housings 100 and 200 are rotated and permanently locked. When the housings 100 and 200 are pushed together, the valves 150 and 250 engage and seal to one another. As illustrated in FIGS. 9 and 10, an operator may push the clip 700 to unlock the stem 230 from the groove 280. The operator may push the flange 270 to axially and proximally move the stem 230. In an alternative example illustrated in FIG. 19, the operator may push the flange 1908 to move the stem 230. The stem 230 may open the path for fluid to flow through by pushing open valves 150 and 250 in the direction of the movement of the stem 230 and to the outside diameter of the stem 230. The flange 270 is pushed until the stem 230 engages the seal 160 and the seal structure 130. The stem 230 is locked into position by rotating and permanently locking the tab 720 and the groove 710, and the stem 230 is sealed with seal 260. As illustrated in FIG. 19, optional tab 1908 may align with an end of the housing 200. An indicator may align to indicate interlocking of the stem 230 and housing 200. The sanitary and sterile connection is complete.

In particular, the connector assembly and method of connecting the assembly may provide advantages over other sterile connectors. For example, the integrity of the sterile environment may be maintained through the stem 230 contacting the seal structure 130 while not being exposed to the environment beyond the sealed apertures 120 and 220. In particular, the stem 230 is configured to move through the valves 150 and 250 without contacting an outside surface of the valves 150 and 250.

Further, the valve 150 or 250 may be configured to open with a desired range of pressure or force, herein called "release pressure." For example, at pressures below the release pressure, the valves 150 or 250 may remain closed and impervious to biological elements, such as bacteria. In particular examples, the valves 150 or 250 are also impervious to fluid, such as liquid, at pressures below the release pressure. At pressures above the release pressures, the valves 150 or 250 may be opened, folding into each other when the connector 10 and 20 are coupled. For example, the release pressure may be in a range of about 3 psi to about 10 psi, such as about 4 psi to about 7 psi, or even about 4.5 psi to about 6 psi.

In another example, the ability to operate the connection may be characterized by a force-to-deploy, defined as the force to push the stem into position. Too great a force, prevents use and too small a force may lead to premature deployment and potential contamination. For example, the force-to-deploy may be in a range of 12 lbf to 30 lbf, such as a range of 15 lbf to 28 lbf, or even a range of 16 lbf to 26 lbf.

In addition, the connector assembly has a pass rating for a Microbial Aerosol Challenge as defined in Example 3 below. The pass rating indicates that the connector assembly can be deployed in contaminated environments and provide an uncontaminated fluid pathway.

In a particular embodiment, the valves 150 or 250 may be formed from an elastomeric material and in particular, an elastomeric material that upon further treatment may re-knit (i.e., the two sides of a cut at least partially heal or bond with less strength than the original un-cut material). For example, the valves may be formed of an elastomeric material, cut to form slits, and then further treated, such as through heating or exposure to actinic radiation. Re-knittable elastomeric materials may at least partially rebind along the slits, resulting in a valve that is impervious to fluids at low pressures, but opens in response to a release force or pressure. In a particular example, the valves 150 or 250 are formed of a silicone polymer, such as a dialkylpolysiloxane. For example, the dialkylpolysiloxane may include alkyl groups, such as methyl, ethyl, propyl or other alkyl groups, or a combination thereof.

In a particular example, the valves 150 or 250 are cut and subsequently heat treated. For example, the cut valves 150 or 250 are heat treated for a period of time in a range of 10 minutes to 1 hour, such as 10 minutes to 30 minutes, or 10 minutes to 20 minutes. Heat treatment may include heat treating at temperatures in a range of 135° C. to 250° C., such as 140° C. to 200° C., or 140° C. to 160° C. In an example, the valve may be assembled into the connector after cutting and the connector and valve may subsequently be heat treated. Alternatively, the valve may be cut and heat treated prior to assembly into the connector.

In an alternative embodiment, the slit may be formed in portions separated by web structures, such as illustrated in FIG. 18. Such web structures may hold the slit closed during transport and handling, while permitting deployment of the connector assembly. In such an embodiment, re-knitting may be avoided.

In a further exemplary embodiment, the connector assembly may incorporate a filter. For example, FIG. 13 includes an illustration of an exemplary housing 1300 in which a filter 1304 is incorporated into a flange 1302. While the illustrated housing 1300 is similar to housing 100, a filter may alternatively be incorporated into the connector portion 20, such as into the flange 270, as illustrated in FIG. 7.

In an example, the filter includes a filter media having a pore size not greater than 2.5 micrometers, such as not greater than 1.0 micrometers. In particular, the filter media may have a pore size not greater than 0.5 micrometers, or even as low as 0.25 micrometers or lower. In an example, the filter media is formed from a polymeric material, such as a hydrophobic polymeric material. In particular, the filter media may be formed of a fluorinated polymer, such as polytetrafluoroethylene.

In a further exemplary embodiment, a portion of the connection is joined to a fitment instead of a tubing connector. For example, FIG. 14, FIG. 15, and FIG. 16 include illustrations of a portion of the connector coupled to a fitment. As illustrated in FIG. 14 and FIG. 15, a connector 1400 is coupled to a fitment 1404. In particular, the connector 1400 may include a flange 1402 that optionally includes a filter 1416. Further, a fluid control valve 1406 may be positioned in the fluid path between the connector 1400 and the fitment 1404. In an example, the fluid control valve 1406 includes a handle 1408. The fluid control valve 1406 may be a ball valve, cock valve or globe valve. Alternatively, the fluid control valve 1406 may be a needle valve or a stop valve.

In an example, the fitment 1404 includes two additional fluid connection ports 1410 and 1412. For example, the fitment 1404 may include an inlet tubing connector 1410 and an outlet tubing connector 1412. Alternatively, the fitment 1404 may include additional connectors similar to connector 1400. While the connector 1400 is illustrated as being similar to connector 10 described above, the connector 1400 may alternatively be configured similar to connector 20.

Figure 16:
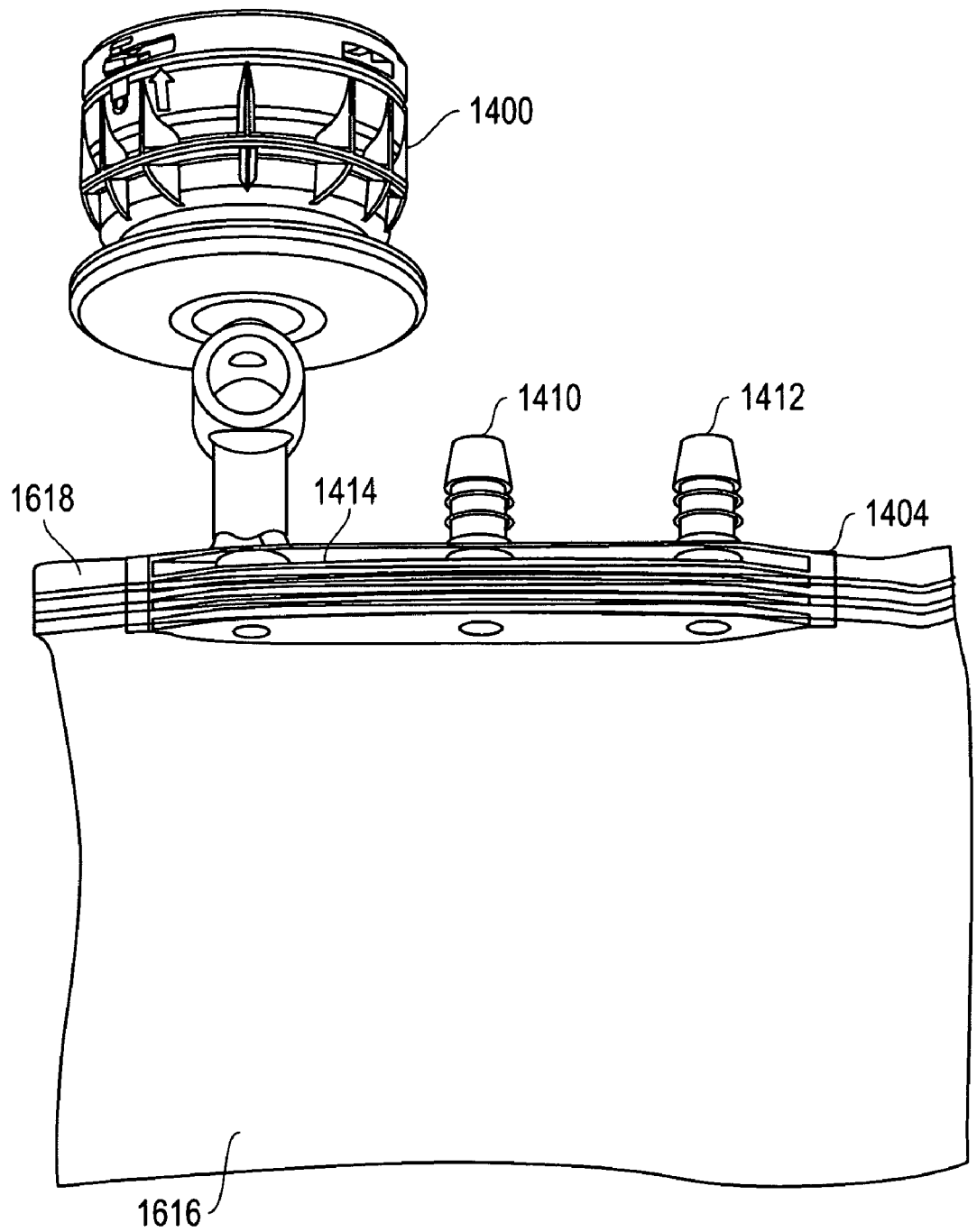

In addition, the fitment 1404 may include ridges 1414 configured to engage a bag or container. As illustrated in FIG. 16, a bag 1616 may be secured to the fitment 1404. In particular, an open end 1618 of the bag 1616 may be placed over the ridges 1414 and heat sealed to the ridges 1414 to close the end 1618 of the bag 1616 around the fitment 1404 and to seal the end 1618 of the bag 1616.

EXAMPLES

Example 1

Sample valves are tested for release pressure. Release pressure is determined as the pressure at which a gas leak or flow through the valve is initially observed. A connector including the valve is attached to a manifold. Alcohol is flooded over the connector on the opposite side of the valve as the manifold connection. Pressure is exerted through the tubing connection of the connector via a pressure regulator. Pressure adjustments are made by 0.1 psi and maintained for 1 minute under observation.

The sample valves are formed of LIM 6045 silicone available from GE Silicones. The valves are molded as illustrated in FIG. 17 and are cut. Each valve is heat treated for 15 minutes at 149° C. Table 1 illustrates the release pressure and observed behavior.

TABLE 1

Release Pressure of Silicone Valves

| Sample No. | Release Pressure (psi) | Comment |
|---|---|---|
| 1 | 5.01 | Valve Opened |
| 2 | 5.53 | Valve Opened |
| 3 | 4.90 | Valve Opened |
| 4 | 5.20 | Valve Opened |
| 5 | 5.40 | Valve Opened |
| 6 | 4.85 | Bubbles at End of Slit |
| 7 | 5.30 | Valve Opened |
| 8 | 5.50 | Valve Opened |
| 9 | 5.25 | Valve Opened |
| 10 | 5.10 | Valve Opened |
| 11 | 4.90 | Valve Opened |
| 12 | 5.60 | Bubbles at End of Slit |
| 13 | 5.25 | Valve Opened |
| 14 | 4.80 | Valve Opened |
| 15 | 5.30 | Valve Opened |
| 16 | 5.65 | Valve Opened |
| 17 | 5.10 | Valve Opened |
| 18 | 4.85 | Bubbles at End of Slit |
| 19 | 5.70 | Bubbles at End of Slit |
| 20 | 5.10 | Valve Opened |
| Avg. | 5.21 | |

Example 2

Samples are tested for contribution of components to force-to-deploy. A first set of samples and a second set of samples are tested to determine the contribution of the valves to force-to-deploy. The samples do not include outer o-ring seals around the stem and are without the ratchet system in place. The first set of samples includes a valve with a slit having two web structures. The samples are post cured for 4 hours at 385° F. before the slit is formed. The second set of samples also includes a valve with a slit having two web structures. The material of the valves includes a fluorosilicone additive and are post cured for 4 hours at 385° F. before the slits are formed.

A third set of samples is tested for contribution of the o-ring to the force-to-deploy. The samples are tested without valves and ratchet systems. A fourth set of samples are tested for contribution of the ratchet system to the force-to-deploy. The samples are free of valves and o-rings. Table 2 illustrates the average force contribution. A total force-to-deploy including one of the valves is in the range of 20.3 and 23.3 lbf.

TABLE 2

Component Force Contribution

| Sample | Average Force (lbf) |
|---|---|
| Valve with Dual Web | 16.47 |
| Valve with Dual Web and Fluorosilicone | 13.60 |
| O-Ring | 3.370 |
| Ratchet System | 3.387 |

Example 3

For this test, 28 samples are tested along with 1 negative control and 1 positive control. The 30 samples are irradiates at 50 kGy prior to testing. The sterile test samples and control samples are prepared by adding a sterile section of tubing to the barbed ends of the inner and outer assemblies in a laminar flow hood. The open ends of the tubing are tightly sealed prior to testing.

A challenge suspension of *Bacillus subtilis* is prepared by making appropriate dilutions in sterile water of injection or sterile distilled water from an original spore suspension so that the aerosol chamber receives a minimum of $4.0 \times 10^7$ spores when aerosolized. The final suspension concentration is verified by plating appropriate dilutions of the suspension to the surface of Trypticase Soy Agar (TSA) via spread plate method. The plates are incubated for a minimum of 24 hours at 30° C.-35° C. A sufficient quantity of Trypticase Soy Broth (TSB) and Fluid D are prepared for the test. A Class 100 laminar flow hood is cleaned and disinfected prior to use and allowed to run for at least 30 minutes before the sterility test.

The 30 samples are removed from their packaging and the unassembled units are placed on a rack in the aerosol chamber. The negative control sample is not exposed to the aerosol challenge. The chamber is sealed and the nebulizers are turned on for one minute. With the chamber fan on, the samples are allowed to sit in the contaminated chamber for 30 minutes. Using the glove ports on the chamber, the inner and outer components are assembled and locked in place. For the positive control sample, an 18 g needle is passed through the wall of the tubing into the fluid path.

After the samples are fully engaged, the nebulizers are refilled with suspension. The second challenge is performed. The nebulizers are pressurized and the suspension is aerosolized until the nebulizers are empty. The samples are allowed to sit in the chamber for one hour, allowing the aerosolized suspension time to challenge the samples.

The chamber fan is turned off and the samples are removed from the chamber. The exterior of each sample is thoroughly disinfected by soaking the parts with a bleach solution. The samples are allowed to sit for a minimum of 1 hour after surface disinfection prior to running the sterility test.

The sterility test is performed by completely flushing the fluid path of the samples with Fluid D and then filtering the rinse through a 0.45 micron membrane filter. The filters are transferred to 100 mL jars to TSB.

The jar samples are incubated at 30° C.-35° C. for a period of 7 days. Evidence of growth is indicated by one or more of the following: turbidity, precipitation or pellicle formation in the jar. The samples that are suspect for microbial growth are analyzed by streaking the suspected contaminant onto TSA and incubating at 30° C.-35° C. Any positive growth is compared to the challenge organism by Gram staining and direct microscopic observation to ensure that the growth is the result of the challenge organism.

Table 3 illustrates that the test samples exhibit no growth, the negative control exhibit no growth, and the positive control exhibit growth of the challenge organism. The test samples act as an effective microbial barrier in maintaining the sterility of the fluid pathway after being exposed to a microbial aerosol challenge. The aerosol is applied twice: prior to assembly and after assembly. Engaging the samples in a contaminated environment did not compromise the sterility of the fluid path.

TABLE 3

Sterility Challenge

| Sample | Growth |
|---|---|
| Tests #1-#28 | No Growth |
| Negative Control | No Growth |
| Positive Control | +(*B. subtilis*) |

In particular, Applicants have discovered particular technical advantages of embodiments of the connector described above. For example, the connector provides protection against undesirable exposure of the internal fluid pathways to external fluids and biological contaminants both prior to and after connection. In addition, the connector permits secure connection of the connectors and engagement of the stem with little force, while limiting accidental exposure of the internal surfaces to biological contamination.

In a first embodiment, a connector assembly includes a first connector and a second connector. The first connector includes a first housing, a seal, and a first valve. The first housing defines a first aperture, a lumen defining a fluid passage therethrough, and a first sealing surface disposed at an end of the lumen. The seal is disposed around the first sealing surface. The first valve is disposed over the first aperture. The second connector includes a stem, a second housing, and a second valve. The stem defines a fluid passage therethrough and defines a second sealing surface at a terminal end of the stem. The second housing surrounds the stem and defines a second aperture. The second housing is configured to engage the first housing of the first connector. The second valve is disposed over the second aperture. The second valve is configured to align with the first valve when the second housing engages the first housing. The stem is to move in relation to the first and second housings and through the first and second valves. The first and second sealing surfaces matingly engage.

In an example of the first embodiment, the second valve is configured to fold with the first valve in a direction of movement of the stem when the stem moves through the first and second valves. In another example, the first valve adheres to the second valve. In a further example, the first or second valves comprise a silicone elastomer, an ethylene propylene diene monomer (EPDM), a thermoplastic elastomer (TPE), or a thermoplastic vulcanizate (TPV).

In another example of the first embodiment, the first valve includes a slit. In an example, the slit is at least partially re-knit. In another example, the slit includes first and second slit portions separated by a web structure. A thickness of the web structure may be in a range of $1/20^{th}$ to $1/40^{th}$ of the length of the first or second slit portion.

In an additional example of the first embodiment, the first sealing surface faces radially outwardly from the lumen and the second sealing surface faces radially inwardly. In an example, the stem does not extend into the lumen. In a particular example, a diameter of the fluid passage varies by not greater than 5% proximal to the matingly engaged first and second sealing surfaces. For example, the diameter of the fluid passage varies by not greater than 1% proximal to the matingly engaged first and second sealing surfaces.

In a further example of the first embodiment, the first connector further includes a filter intersecting the lumen and fluid passage. In another example, a fitment is coupled to first connector and providing fluid communication with the fluid passage. In an additional example, a bag is coupled to the fitment. For example, the fitment may include two tubing connectors providing second and third fluid passages. In another example, the fitment includes ridges to engage an end of a bag.

In an additional example of the first embodiment, the connector assembly has a pass rating for the Microbial Aerosol Challenge. In another example, the connector assembly has a force-to-deploy in a range of 12 lbf to 30 lbf.

In a second embodiment, a connector assembly includes first and second connectors. The first connector includes a first housing, a seal, and a first valve. The first housing defines a first aperture, a lumen defining a fluid passage therethrough, and a first sealing surface disposed at an end of the lumen. The first sealing surface faces radially outwardly and forms a separate surface from a surface defining the lumen. The seal is disposed around the first sealing surface. The first valve is disposed over the first aperture. The second connector includes a stem, a second housing, and a second valve. The stem defines a fluid passage therethrough and defines a second sealing surface at a terminal end of the stem. The second sealing surface faces radially inwardly and forms a separate surface from an inner surface of the stem. The second housing surrounds the stem and defines a second aperture. The second housing is configured to engage the first housing of the first connector. The second valve is disposed over the second aperture. The second valve is configured to align with the first valve when the second housing engages the first housing. The stem is to move in relation to the first and second housings and through the first and second valves. The first and second sealing surfaces are to matingly engage.

In a third embodiment, a connector assembly includes first and second connectors. The first connector includes a stem, a first housing, and a first valve. The stem defines a fluid passage therethrough and defines a first sealing surface at a terminal end of the stem. The first housing surrounds the stem and defines a first aperture. The stem is movable relative to the first housing. The first valve is disposed over the first aperture. The first valve includes a slit and a set of ridges disposed on a side of the first valve in proximity to the stem. The second connector includes a second housing defining a fluid passage therethrough and defining a second sealing surface to engage the first sealing surface of the stem. The ridges are configured to open the slit without the terminal end of the stem contacting the slit when the stem moves through the first valve contacts the ridges.

In an example of the third embodiment, the second connector further includes a second valve. The second housing defines a second aperture over which the second valve is disposed. The second valve is configured to open and fold with the first valve in response to the stem moving through the first valve.

In a fourth embodiment, a connector assembly includes first and second connectors. The first connector includes a stem, a first housing and a first valve. The stem defines a fluid passage therethrough and defines a first sealing surface at a terminal end of the stem. The first housing surrounds the stem and defines a first aperture. The stem is movable relative to the first housing. The first valve is disposed over the first aperture. The first valve includes a slit including first and second slit portions separated by a web structure. The second connector includes a second housing defining a fluid passage therethrough and defining a second sealing surface to engage the first sealing surface of the stem. The web structure is configured to hold the slit closed until the stem moves through the first valve.

In a fifth embodiment, a method of forming a sterile connection includes engaging a first housing of a first connector to a second housing of a second connector, the first connector includes the first housing, a seal, and a first valve. The first housing defines a first aperture, a lumen defining a fluid passage therethrough, and a first sealing surface disposed at an end of the lumen. The seal is disposed around the first sealing surface. The first valve is disposed over the first aperture. The second connector includes a stem, the second housing, and a second valve. The stem defines a fluid passage therethrough and defines a second sealing surface at a terminal end of the stem. The second housing surrounds the stem and defines a second aperture. The second housing is configured to engage the first housing of the first connector. The second valve is disposed over the second aperture. The second valve is configured to align with the first valve when the second housing engages the first housing. The method further includes pushing the stem through the first and second valves. The first and second valves fold together in the direction in which the stem is pushed. In addition, the method includes contacting the first sealing surface to the second sealing surface.

In an example of the fifth embodiment, the method also includes interlocking the stem to the second housing. In another example, the method further includes disengaging an interlocking mechanism prior to pushing the stem. In an additional example, engaging the first and second housings includes inserting the second housing into the first housing and twisting the first housing relative to the second housing to interlock the first and second housings. In a further example, pushing the stem includes pushing against the force of a ratchet system. In an additional example, pushing the stem causes the terminal end of the stem to contact ridges of the second valve, opening a slit in the valve without the terminal end of the stem contacting the slit. In another example, pushing the stem causes a web structure of the slit to break.

In a sixth embodiment, a system of interconnected vessels includes a first vessel connected to a tubing and a connector assembly. The connector assembly includes first and second connectors. The first connector includes a first housing, a seal, and a first valve. The first housing defines a first aperture, a lumen defining a fluid passage therethrough, and a first sealing surface disposed at an end of the lumen. The seal is disposed around the first sealing surface. The first valve is disposed over the first aperture. The second connector includes a stem, a second housing, and a second valve. The stem defines a fluid passage therethrough and defines a second sealing surface at a terminal end of the stem. The stem is connected to the tubing. The second housing surrounds the stem and defines a second aperture. The second housing is configured to engage the first housing of the first connector. The second valve is disposed over the second aperture. The second valve is configured to align with the first valve when the second housing engages the first housing. The stem is to move in relation to the first and second housings and through the first and second valves. The first and second sealing surfaces matingly engage.

In an example of the sixth embodiment, the system further includes a second vessel connected to second tubing. The second tubing is connected to the first housing. In an additional example, the first housing forms a fitment of a bag.

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

As used herein, the terms "comprises," "comprising," "includes," "including," "has," "having" or any other variation thereof, are intended to cover a non-exclusive inclusion. For example, a process, method, article, or apparatus that comprises a list of features is not necessarily limited only to those features but may include other features not expressly listed or inherent to such process, method, article, or apparatus. Further, unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present).

Also, the use of "a" or "an" are employed to describe elements and components described herein. This is done merely for convenience and to give a general sense of the scope of the invention. This description should be read to include one or at least one and the singular also includes the plural unless it is obvious that it is meant otherwise.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

After reading the specification, skilled artisans will appreciate that certain features are, for clarity, described herein in the context of separate embodiments, may also be provided in combination in a single embodiment. Conversely, various features that are, for brevity, described in the context of a single embodiment, may also be provided separately or in any subcombination. Further, references to values stated in ranges include each and every value within that range.

What is claimed is:

1. A connector assembly comprising:
   a first connector comprising:
      a first housing defining a first aperture, a lumen defining a fluid passage therethrough, and a first sealing surface disposed at an end of the lumen;
      a seal disposed around the first sealing surface; and
      a first valve disposed over the first aperture; and
   a second connector comprising:
      a stem defining a fluid passage therethrough and defining a second sealing surface at a terminal end of the stem;
      a second housing surrounding the stem and defining a second aperture, wherein the second housing is configured to engage the first housing of the first connector; and
      a second valve disposed over the second aperture, wherein the second valve is configured to align with the first valve when the second housing engages the first housing;
   wherein the stem is to move in relation to the first and second housings and through the first and second valves, the first and second sealing surfaces to matingly engage;
   wherein the first sealing surface faces radially outwardly from the lumen and wherein the second sealing surface faces radially inwardly.

2. The connector assembly of claim 1, wherein the second valve is configured to fold with the first valve in a direction of movement of the stem when the stem moves through the first and second valves.

3. The connector assembly of claim 1, wherein the first valve adheres to the second valve.

4. The connector assembly of claim 1, wherein the first or second valves comprise a silicone elastomer, an ethylene propylene diene monomer (EPDM), a thermoplastic elastomer (TPE), or a thermoplastic vulcanizate (TPV).

5. The connector assembly of claim 1, wherein the stem does not extend into the lumen.

6. The connector assembly of claim 1, wherein a diameter of the fluid passage varies by not greater than 5% proximal to the matingly engaged first and second sealing surfaces.

7. The connector assembly of claim 1, wherein the first connector further comprises a filter intersecting the lumen and fluid passage.

8. The connector assembly of claim 1, further comprising a fitment coupled to first connector and providing fluid communication with the fluid passage.

9. The connector assembly of claim 1, wherein the connector assembly has a pass rating for the Microbial Aerosol Challenge.

10. A connector assembly comprising:
    a first connector comprising:
       a first housing defining a first aperture, a lumen defining a fluid passage therethrough, and a first sealing surface disposed at an end of the lumen;
       a seal disposed around the first sealing surface; and
       a first valve disposed over the first aperture; and
    a second connector comprising:
       a stem defining a fluid passage therethrough and defining a second sealing surface at a terminal end of the stem;
       a second housing surrounding the stem and defining a second aperture, wherein the second housing is configured to engage the first housing of the first connector; and
       a second valve disposed over the second aperture, wherein the second valve is configured to align with the first valve when the second housing engages the first housing;
    wherein the stem is to move in relation to the first and second housings and through the first and second valves, the first and second sealing surfaces to matingly engage;
    wherein the first valve includes a slit;
    wherein the slit includes first and second slit portions separated by a web structure.

11. The connector assembly of claim 10, wherein the slit is at least partially re-knit.

12. The connector assembly of claim 10, wherein a thickness of the web structure is in a range of $1/20^{th}$ to $1/40^{th}$ of the length of the first or second slit portion.

13. A method of forming a sterile connection, the method comprising:
engaging a first housing of a first connector to a second housing of a second connector, the first connector comprising:
the first housing defining a first aperture, a lumen defining a fluid passage therethrough, and a first sealing surface disposed at an end of the lumen;
a seal disposed around the first sealing surface; and
a first valve disposed over the first aperture;
the second connector comprising:
a stem defining a fluid passage therethrough and defining a second sealing surface at a terminal end of the stem;
the second housing surrounding the stem and defining a second aperture, wherein the second housing is configured to engage the first housing of the first connector; and
a second valve disposed over the second aperture, wherein the second valve is configured to align with the first valve when the second housing engages the first housing;
pushing the stem through the first and second valves, the first and second valves folding together in the direction in which the stem is pushed, wherein pushing the stem causes the terminal end of the stem to contact ridges of the second valve, opening a slit in the valve without the terminal end of the stem contacting the slit; and
contacting the first sealing surface to the second sealing surface.

14. The method of claim 13, wherein pushing the stem causes a web structure of the slit to break.

15. A system of interconnected vessels comprising:
a first vessel connected to a tubing; and
a connector assembly comprising:
a first connector comprising:
a first housing defining a first aperture, a lumen defining a fluid passage therethrough, and a first sealing surface disposed at an end of the lumen;
a seal disposed around the first sealing surface; and
a first valve disposed over the first aperture; and
a second connector comprising:
a stem defining a fluid passage therethrough and defining a second sealing surface at a terminal end of the stem, the stem connected to the tubing;
a second housing surrounding the stem and defining a second aperture, wherein the second housing is configured to engage the first housing of the first connector; and
a second valve disposed over the second aperture, wherein the second valve is configured to align with the first valve when the second housing engages the first housing;
wherein the stem is to move in relation to the first and second housings and through the first and second valves, the first and second sealing surfaces to matingly engage;
wherein the first sealing surface faces radially outwardly from the lumen and wherein the second sealing surface faces radially inwardly.

16. The system of claim 15, further comprising a second vessel connected to second tubing, the second tubing connected to the first housing.

17. The system of claim 15, wherein the first housing forms a fitment of a bag.

* * * * *